United States Patent
Scott et al.

(10) Patent No.: US 11,355,220 B2
(45) Date of Patent: *Jun. 7, 2022

(54) LABORATORY CENTRAL CONTROL UNIT METHOD AND SYSTEM

(71) Applicant: BECTON DICKINSON AND COMPANY, Franklin Lakes, NJ (US)

(72) Inventors: John Scott, Damascus, MD (US); Lauren Hannon, Arlington, VA (US); Jason Troxell, Hagerstown, MD (US); Emmet Brown, Dickerson, MD (US)

(73) Assignee: BECTON, DICKINSON AND COMPANY, Franklin Lakes, NJ (US)

(*) Notice: Subject to any disclaimer, the term of this patent is extended or adjusted under 35 U.S.C. 154(b) by 923 days.

This patent is subject to a terminal disclaimer.

(21) Appl. No.: 15/935,761

(22) Filed: Mar. 26, 2018

(65) Prior Publication Data

US 2018/0226139 A1 Aug. 9, 2018

Related U.S. Application Data

(63) Continuation of application No. 12/949,503, filed on Nov. 18, 2010, now Pat. No. 9,953,141.

(60) Provisional application No. 61/262,497, filed on Nov. 18, 2009.

(51) Int. Cl.
*G16H 10/40* (2018.01)
*G16H 10/60* (2018.01)

(52) U.S. Cl.
CPC ............ *G16H 10/40* (2018.01); *G16H 10/60* (2018.01)

(58) Field of Classification Search
None
See application file for complete search history.

(56) References Cited

U.S. PATENT DOCUMENTS

| | | |
|---|---|---|
| 2,360,378 A | 10/1944 | Putter |
| 2,979,210 A | 4/1961 | Patterson |
| 3,375,934 A | 4/1968 | Bates |
| 3,379,315 A | 4/1968 | Broadwin |
| 3,491,894 A | 1/1970 | Brown |
| 3,589,103 A | 6/1971 | Calvillo |
| 3,744,665 A | 7/1973 | Spoto |
| 3,905,482 A | 9/1975 | Knulst |
| 3,918,920 A | 11/1975 | Barber |
| 4,000,976 A | 1/1977 | Kramer et al. |
| 4,039,286 A | 8/1977 | Keller et al. |
| 4,068,798 A | 1/1978 | Rohde |
| 4,096,965 A | 6/1978 | Lessnig et al. |
| 4,124,122 A | 11/1978 | Emmitt |
| 4,151,950 A | 5/1979 | Gunnewig |
| 4,217,798 A | 8/1980 | McCarthy |
| 4,224,278 A | 9/1980 | Hogen Esch |
| 4,283,950 A | 8/1981 | Tervamaki |
| 4,338,279 A | 7/1982 | Orimo et al. |
| 4,368,913 A | 1/1983 | Brockmann et al. |
| 4,406,547 A | 9/1983 | Aihara |
| 4,478,095 A | 10/1984 | Bradley |
| 4,482,522 A | 11/1984 | Baudisch et al. |
| 4,483,927 A | 11/1984 | Takekawa |
| 4,517,160 A | 5/1985 | Galle et al. |
| 4,534,465 A | 8/1985 | Rothermel et al. |
| 4,535,585 A | 8/1985 | Gardos |
| 4,544,193 A | 10/1985 | Dunn et al. |
| 4,545,723 A | 10/1985 | Clark |
| 4,609,017 A | 9/1986 | Coulter et al. |
| 4,632,631 A | 12/1986 | Dunlap |
| 4,692,308 A | 9/1987 | Riley et al. |
| 4,696,144 A | 9/1987 | Bankuty |
| 4,740,025 A | 4/1988 | Nelson |
| 4,766,082 A | 8/1988 | Marteau D'Autry |
| 4,794,085 A | 12/1988 | Jessop |
| 4,798,095 A | 1/1989 | Itoh |
| 4,805,772 A | 2/1989 | Shaw et al. |
| 4,855,110 A | 8/1989 | Marker |
| 4,856,073 A | 8/1989 | Farber et al. |
| 4,861,553 A | 8/1989 | Mawhirt et al. |
| 4,876,926 A | 10/1989 | Muszak |
| 4,938,369 A | 7/1990 | Carilli |
| 4,968,077 A | 11/1990 | Redmon et al. |

(Continued)

FOREIGN PATENT DOCUMENTS

| | | |
|---|---|---|
| EP | 0979999 | 2/2000 |
| JP | 2184762 | 7/1990 |

(Continued)

OTHER PUBLICATIONS

International Search Report from PCT/US09/064258 dated Jan. 6, 2010.

(Continued)

*Primary Examiner* — Channing S Mahatan

(74) *Attorney, Agent, or Firm* — Botos Churchill IP Law LLP

(57) ABSTRACT

A method for coordinating data between a plurality of sample processing systems is disclosed. In some implementations, the method comprises providing, using a central control unit, data to a pre-analytical sample processing system identifying a sample undergoing pre-analytical processing, receiving data, at the central control unit, indicating the transfer of the sample to an analytical system, providing, from the central control unit (CCU), data associated with the sample to the analytical system, and receiving a result associated with the sample from the analytical system.

23 Claims, 32 Drawing Sheets

(56) References Cited

U.S. PATENT DOCUMENTS

| | | |
|---|---|---|
| 4,970,053 A | 11/1990 | Fechtner |
| 4,974,460 A | 12/1990 | Baxter |
| 4,982,553 A | 1/1991 | Itoh |
| 5,008,081 A | 4/1991 | Blau et al. |
| 5,008,082 A | 4/1991 | Shaw |
| 5,013,529 A | 5/1991 | Itoh |
| 5,063,790 A | 11/1991 | Freeman |
| 5,075,082 A | 12/1991 | Fechtner |
| 5,080,232 A | 1/1992 | Leoncavallo et al. |
| 5,080,864 A | 1/1992 | Shaw |
| 5,087,423 A | 2/1992 | Ishibashi |
| 5,116,578 A | 5/1992 | Baxter |
| 5,137,693 A | 8/1992 | Mawhirt |
| 5,174,762 A | 12/1992 | Hoppal |
| 5,202,262 A | 4/1993 | Lemonnier |
| 5,203,236 A | 4/1993 | Anderson |
| 5,232,665 A | 8/1993 | Burkovich et al. |
| 5,255,574 A | 10/1993 | Wuerschum |
| 5,270,210 A | 12/1993 | Weyrauch et al. |
| 5,271,897 A | 12/1993 | Wurschum |
| 5,313,858 A | 5/1994 | Stitt |
| 5,332,549 A | 7/1994 | MacIndoe, Jr. |
| 5,340,544 A | 8/1994 | Nishikawa |
| 5,341,854 A | 8/1994 | Zezuika |
| 5,366,896 A | 11/1994 | Margrey |
| 5,374,395 A | 12/1994 | Robinson |
| 5,389,339 A | 2/1995 | Petschek et al. |
| 5,397,542 A | 3/1995 | Nelms et al. |
| 5,417,922 A | 5/1995 | Markin et al. |
| 5,437,838 A | 8/1995 | DeMoranville |
| 5,445,037 A | 8/1995 | Itoh |
| 5,456,887 A | 10/1995 | Calvo et al. |
| 5,463,895 A | 11/1995 | Brentz |
| 5,472,669 A | 12/1995 | Miki et al. |
| 5,479,869 A | 1/1996 | Coudon et al. |
| 5,481,946 A | 1/1996 | Nishikawa |
| 5,490,321 A | 2/1996 | Kaneko |
| 5,491,067 A | 2/1996 | Setcavage et al. |
| 5,493,849 A | 2/1996 | Itoh |
| 5,499,545 A | 3/1996 | Kimura |
| 5,503,036 A | 4/1996 | Nguyen |
| 5,525,298 A | 6/1996 | Anami |
| 5,536,056 A | 7/1996 | Clarke et al. |
| 5,537,880 A | 7/1996 | Takeda |
| 5,540,081 A | 7/1996 | Takeda |
| 5,540,890 A | 7/1996 | Clark |
| 5,550,059 A | 8/1996 | Boger |
| 5,551,828 A | 9/1996 | Lies |
| 5,578,494 A | 11/1996 | Clark |
| 5,579,929 A | 12/1996 | Schwartz |
| 5,585,068 A | 12/1996 | Panetz et al. |
| 5,589,137 A | 12/1996 | Markin et al. |
| 5,604,101 A | 2/1997 | Hanley |
| 5,627,522 A | 5/1997 | Walker |
| 5,637,275 A | 6/1997 | Carey |
| 5,639,599 A | 6/1997 | Ryder et al. |
| 5,646,049 A | 7/1997 | Tayi |
| 5,651,941 A | 7/1997 | Stark et al. |
| 5,652,568 A | 7/1997 | Ko |
| 5,658,532 A | 8/1997 | Kurosaki et al. |
| 5,675,715 A | 10/1997 | Bernstein |
| 5,687,849 A | 11/1997 | Borenstein et al. |
| 5,700,429 A | 12/1997 | Buhler et al. |
| 5,721,384 A | 2/1998 | Tanihata |
| 5,723,289 A | 3/1998 | Eaton |
| 5,730,276 A | 3/1998 | Itoh |
| 5,736,102 A | 4/1998 | Seaton |
| 5,737,498 A | 4/1998 | Murray |
| 5,753,186 A | 5/1998 | Hanley |
| 5,772,962 A | 6/1998 | Uchida et al. |
| 5,775,755 A | 7/1998 | Covert et al. |
| 5,778,740 A | 7/1998 | Tye |
| 5,814,276 A | 9/1998 | Riggs |
| 5,819,508 A | 10/1998 | Kraft |
| 5,851,042 A | 12/1998 | Bankuty et al. |
| 5,861,563 A | 1/1999 | Boyd |
| 5,872,361 A | 2/1999 | Paoli et al. |
| 5,876,670 A | 3/1999 | Mitsumaki |
| 5,882,596 A | 3/1999 | Breeser et al. |
| 5,897,835 A | 4/1999 | Seaton |
| 5,915,282 A | 6/1999 | Merriam |
| 5,919,706 A | 7/1999 | Tajima |
| 5,928,952 A | 7/1999 | Hutchins et al. |
| 5,948,360 A | 9/1999 | Rao et al. |
| 5,965,828 A | 10/1999 | Merriam |
| 5,966,309 A | 10/1999 | OBryan |
| 5,985,219 A | 11/1999 | Lind |
| 5,985,672 A | 11/1999 | Kegelman |
| 5,988,857 A | 11/1999 | Ozawa |
| 5,996,818 A | 12/1999 | Boje et al. |
| 6,022,747 A | 2/2000 | Gherson |
| 6,060,022 A | 5/2000 | Pang et al. |
| 6,060,320 A | 5/2000 | Dorenkott |
| 6,065,617 A | 5/2000 | Cohen |
| 6,071,477 A | 6/2000 | Auclair et al. |
| 6,076,330 A | 6/2000 | Thomas |
| 6,100,094 A | 8/2000 | Tajima |
| 6,105,343 A | 8/2000 | Grove |
| 6,111,238 A | 8/2000 | Fix et al. |
| 6,117,398 A | 9/2000 | Bienhaus |
| 6,121,049 A | 9/2000 | Dorenkott |
| 6,123,205 A | 9/2000 | Dumitrescu et al. |
| 6,126,903 A | 10/2000 | Preston |
| 6,141,602 A | 10/2000 | Igarashi |
| 6,142,039 A | 11/2000 | Herring, Sr. |
| 6,156,275 A | 12/2000 | Dumitrescu et al. |
| 6,156,575 A | 12/2000 | Fassbind |
| 6,161,759 A | 12/2000 | Moss et al. |
| 6,170,232 B1 | 1/2001 | VandeGeijn |
| 6,190,619 B1 | 2/2001 | Kilcoin |
| 6,202,278 B1 | 3/2001 | Nakayama |
| 6,203,760 B1 | 3/2001 | Van Der Plaats et al. |
| 6,216,340 B1 | 4/2001 | Fassbind |
| 6,227,053 B1 | 5/2001 | Purpura et al. |
| 6,232,464 B1 | 5/2001 | Lange |
| 6,257,091 B1 | 7/2001 | Cohen et al. |
| 6,274,092 B1 | 8/2001 | Itoh |
| 6,290,907 B1 | 9/2001 | Takahashi |
| 6,293,750 B1 | 9/2001 | Cohen et al. |
| 6,299,840 B1 | 10/2001 | Watanabe et al. |
| 6,321,619 B1 | 11/2001 | Itoh |
| 6,326,147 B1 | 12/2001 | Oldham |
| 6,331,437 B1 | 12/2001 | Cohen |
| 6,332,636 B1 | 12/2001 | Cohen |
| 6,335,166 B1 | 1/2002 | Ammann |
| 6,347,552 B1 | 2/2002 | Purpura |
| 6,358,474 B1 | 3/2002 | Dobler |
| 6,370,942 B1 | 4/2002 | Dunfee |
| 6,415,669 B1 | 7/2002 | Carl |
| 6,417,008 B2 | 7/2002 | Tyberg |
| 6,426,228 B1 | 7/2002 | Cohen et al. |
| 6,432,365 B1 | 8/2002 | Levin et al. |
| 6,435,582 B1 | 8/2002 | Dasilva et al. |
| 6,436,349 B1 | 8/2002 | Carey |
| 6,444,472 B1 | 9/2002 | Cohen et al. |
| 6,449,827 B1 | 9/2002 | Clarke |
| 6,458,324 B1 | 10/2002 | Schinzel |
| 6,484,556 B1 | 11/2002 | Jabobs |
| 6,498,037 B1 | 12/2002 | Carey |
| 6,499,364 B1 | 12/2002 | Suovaniemi |
| 6,521,183 B1 | 2/2003 | Burri et al. |
| 6,531,096 B1 | 3/2003 | Deveney |
| 6,553,824 B1 | 4/2003 | Lutze |
| 6,558,628 B1 | 5/2003 | Reo |
| 6,562,299 B1 | 5/2003 | Ostgaard |
| 6,562,568 B1 | 5/2003 | Kleiber |
| 6,565,809 B1 | 5/2003 | Itoh |
| 6,572,824 B1 | 6/2003 | Ostgaard |
| 6,573,088 B2 | 6/2003 | Gemmell |
| 6,576,477 B1 | 6/2003 | Tokiwa |
| 6,581,647 B1 | 6/2003 | Leidlein |
| 6,598,474 B2 | 7/2003 | Purpura et al. |
| 6,599,476 B1 | 7/2003 | Watson et al. |
| 6,604,337 B2 | 8/2003 | Close |

(56) References Cited

U.S. PATENT DOCUMENTS

| | | |
|---|---|---|
| 6,604,903 B2 | 8/2003 | Osborne |
| 6,605,213 B1 | 8/2003 | Ammann |
| 6,620,585 B1 | 9/2003 | Zyskind |
| 6,622,578 B2 | 9/2003 | Carl |
| 6,651,305 B2 | 11/2003 | Fassbind |
| 6,656,724 B1 | 12/2003 | Heimberg |
| 6,669,910 B1 | 12/2003 | Bienhaus et al. |
| 6,689,318 B1 | 2/2004 | Spork |
| 6,691,748 B1 | 2/2004 | Tajima |
| 6,721,615 B2 | 4/2004 | Fava |
| 6,723,289 B2 | 4/2004 | Iheme |
| 6,730,517 B1 | 5/2004 | Koster |
| 6,734,424 B2 | 5/2004 | Lennon |
| 6,743,398 B2 | 6/2004 | Itoh |
| 6,764,649 B2 | 7/2004 | Ammann |
| 6,772,650 B2 | 8/2004 | Ohyama |
| 6,773,927 B2 | 8/2004 | Osawa |
| 6,793,887 B2 | 9/2004 | Itoh |
| 6,805,294 B2 | 10/2004 | Itoh |
| 6,810,757 B2 | 11/2004 | Carl |
| 6,829,954 B2 | 12/2004 | Katagi |
| 6,838,051 B2 | 1/2005 | Marquiss et al. |
| 6,843,357 B2 | 1/2005 | Bybee et al. |
| 6,849,236 B2 | 2/2005 | Spitz |
| 6,852,283 B2 | 2/2005 | Acosta |
| 6,864,100 B1 | 3/2005 | Ribbe et al. |
| 6,871,566 B2 | 3/2005 | Niwayama |
| 6,887,432 B2 | 5/2005 | Kansy et al. |
| 6,890,742 B2 | 5/2005 | Ammann |
| 6,919,044 B1 | 7/2005 | Shibata et al. |
| 6,919,175 B1 | 7/2005 | Bienhaus |
| 6,926,058 B2 | 8/2005 | Sato |
| 6,938,504 B2 | 9/2005 | Camenisch |
| 6,943,181 B2 | 9/2005 | Sundermann |
| 6,956,055 B2 | 10/2005 | Sundermann |
| 6,959,952 B2 | 11/2005 | Williams |
| 6,978,689 B2 | 12/2005 | Carl |
| 6,984,527 B2 | 1/2006 | Miller |
| 6,985,828 B2 | 1/2006 | Itoh |
| 6,998,094 B2 | 2/2006 | Haslam |
| 7,000,785 B2 | 2/2006 | Jafari et al. |
| 7,078,698 B2 | 7/2006 | Itoh |
| 7,087,607 B2 | 8/2006 | Gerlach |
| 7,117,902 B2 | 10/2006 | Osborne |
| 7,118,892 B2 | 10/2006 | Ammann et al. |
| 7,141,213 B1 | 11/2006 | Pang et al. |
| 7,150,190 B2 | 12/2006 | Krufka |
| 7,152,504 B2 | 12/2006 | Itoh |
| 7,152,736 B1 | 12/2006 | Menichini |
| 7,159,489 B2 | 1/2007 | Itoh |
| 7,207,241 B2 | 4/2007 | Itoh |
| 7,220,385 B2 | 5/2007 | Blecka et al. |
| 7,227,622 B2 | 6/2007 | Itoh |
| 7,233,838 B2 | 6/2007 | Barry et al. |
| 7,251,921 B2 | 8/2007 | Galimberti |
| 7,282,182 B2 | 10/2007 | Dale |
| 7,284,900 B2 | 10/2007 | Mayer |
| 7,287,792 B2 | 10/2007 | Tye |
| 7,322,170 B2 | 1/2008 | Tomalesky |
| 7,340,324 B2 | 3/2008 | Heath et al. |
| 7,377,027 B2 | 5/2008 | Mayer |
| 7,409,809 B1 | 8/2008 | Degen |
| 7,416,706 B2 | 8/2008 | Brunner |
| 7,421,831 B2 | 9/2008 | Neeper |
| 7,425,305 B2 | 9/2008 | Itoh |
| 7,435,387 B2 | 10/2008 | Itoh |
| 7,477,997 B2 | 1/2009 | Kapiit |
| 7,501,094 B2 | 3/2009 | Bysouth |
| 7,514,042 B2 | 4/2009 | Lihl et al. |
| 7,537,735 B2 | 5/2009 | Hiemer |
| 7,556,777 B2 | 7/2009 | Victor |
| 7,572,638 B2 | 8/2009 | Pressman |
| 7,575,937 B2 | 8/2009 | Wiggli |
| 7,579,190 B2 | 8/2009 | Ostgaard |
| 7,581,660 B2 | 9/2009 | Nay |
| 7,597,846 B2 | 10/2009 | Walter et al. |
| 7,610,115 B2 | 10/2009 | Rob et al. |
| 7,634,378 B2 | 12/2009 | Kaplit |
| 7,635,246 B2 | 12/2009 | Neeper |
| 7,681,466 B2 | 3/2010 | Miller |
| 7,694,591 B2 | 4/2010 | Leibfried |
| 7,783,383 B2 | 8/2010 | Eliuk |
| 7,792,647 B1 | 9/2010 | Ding |
| 7,846,384 B2 | 12/2010 | Watson et al. |
| 7,858,033 B2 | 12/2010 | Itoh |
| 7,985,375 B2 | 7/2011 | Edens et al. |
| 8,099,928 B2 | 1/2012 | Yuyama |
| 8,932,942 B2 | 1/2015 | Steinmann |
| 9,953,141 B2 * | 4/2018 | Scott .................. G16H 10/40 |
| 2002/0001542 A1 | 1/2002 | Itoh |
| 2002/0025064 A1 | 2/2002 | Itoh |
| 2002/0041828 A1 | 4/2002 | Spitz |
| 2002/0086431 A1 | 7/2002 | Markham et al. |
| 2002/0090320 A1 | 7/2002 | Burow et al. |
| 2002/0125230 A1 | 9/2002 | Aight et al. |
| 2002/0164269 A1 | 11/2002 | Ngo et al. |
| 2002/0186363 A1 | 12/2002 | Samsoondar et al. |
| 2003/0061911 A1 | 4/2003 | Niwayama |
| 2003/0069699 A1 | 4/2003 | Ekins et al. |
| 2003/0092186 A1 | 5/2003 | Pressman et al. |
| 2003/0213313 A1 | 11/2003 | Katagi |
| 2003/0215362 A1 | 11/2003 | Sato |
| 2004/0022682 A1 | 2/2004 | Itoh |
| 2004/0029135 A1 | 2/2004 | Ramberg |
| 2004/0076546 A1 | 4/2004 | Bissett |
| 2004/0171168 A1 | 9/2004 | Itoh |
| 2004/0184958 A1 | 9/2004 | Itoh |
| 2004/0184959 A1 | 9/2004 | Itoh |
| 2004/0209374 A1 | 10/2004 | Kopf-Sill et al. |
| 2005/0037502 A1 | 2/2005 | Miller |
| 2005/0047966 A1 | 3/2005 | Itoh |
| 2005/0069913 A1 | 3/2005 | Mian et al. |
| 2005/0158212 A1 | 7/2005 | Yavilevich |
| 2005/0252342 A1 | 11/2005 | Itoh |
| 2006/0115889 A1 | 6/2006 | Nakashima |
| 2006/0136095 A1 | 6/2006 | Rob et al. |
| 2006/0210432 A1 | 9/2006 | Victor |
| 2007/0000352 A1 | 1/2007 | Itoh |
| 2007/0006550 A1 | 1/2007 | Kemper |
| 2007/0020764 A1 | 1/2007 | Miller |
| 2007/0059209 A1 | 3/2007 | Pang |
| 2007/0095024 A1 | 5/2007 | Neeper |
| 2007/0172396 A1 | 7/2007 | Neeper |
| 2007/0254277 A1 | 11/2007 | Scrabeck |
| 2008/0019878 A1 | 1/2008 | Trump |
| 2008/0022808 A1 | 1/2008 | Owen |
| 2008/0038827 A1 | 2/2008 | Miller |
| 2008/0069730 A1 | 3/2008 | Itoh |
| 2008/0090288 A1 | 4/2008 | Hibino |
| 2008/0160539 A1 | 7/2008 | Murphy et al. |
| 2008/0160599 A1 | 7/2008 | Weber-Matthiesen |
| 2008/0170967 A1 | 7/2008 | Itoh |
| 2008/0247914 A1 | 10/2008 | Edens et al. |
| 2009/0003981 A1 | 1/2009 | Miller |
| 2009/0028754 A1 | 1/2009 | Robb |
| 2009/0068062 A1 * | 3/2009 | Jafari .................. G01N 35/1016 422/64 |
| 2009/0098022 A1 | 4/2009 | Tokhtuev et al. |
| 2009/0117620 A1 | 5/2009 | Fritchie et al. |
| 2009/0266149 A1 | 10/2009 | Kaplit |
| 2009/0305392 A1 | 12/2009 | Alfredsson et al. |
| 2009/0318276 A1 | 12/2009 | Miller |
| 2010/0015007 A1 | 1/2010 | Pedrazzini |
| 2010/0105060 A1 | 4/2010 | Eder et al. |
| 2010/0159463 A1 | 6/2010 | Eder et al. |
| 2010/0215548 A1 | 8/2010 | Deluca |
| 2010/0241270 A1 | 9/2010 | Eliuk |

FOREIGN PATENT DOCUMENTS

| | | |
|---|---|---|
| WO | 2006054964 | 5/2006 |
| WO | 2006081612 | 8/2006 |
| WO | WO2007/048042 | 4/2007 |
| WO | 2008011312 | 1/2008 |

(56) References Cited

FOREIGN PATENT DOCUMENTS

| | | |
|---|---|---|
| WO | WO2008/123882 | 10/2008 |
| WO | 2009068555 | 6/2009 |
| WO | 2010038852 | 4/2010 |
| WO | 2010056884 | 5/2010 |
| WO | 2010056890 | 5/2010 |
| WO | 2010056903 | 5/2010 |
| WO | 2010057861 | 5/2010 |
| WO | 2010141040 | 12/2010 |
| WO | WO2011/063139 | 5/2011 |

OTHER PUBLICATIONS

International Search Report from PCT/US09/064268 dated Mar. 10, 2010.
International Search Report from PCT/US09/64236 dated Jan. 27, 2010.
International Search Report from PCT/US09/64244 dated Jan. 26, 2010.
Entire patent prosecution history of U.S. Appl. No. 12/062,950, filed Apr. 4, 2008, entitled, "Sample Preparation System and Method for Processing Clinical Specimens," now U.S. Pat. No. 7,985,375, issued Jul. 26, 2011.
Entire patent prosecution history of U.S. Appl. No. 12/588,304, filed Oct. 9, 2009, entitled, "Automated Assay and System," now U.S. Pat. No. 8,357,538, issued Jan. 22, 2013.
Entire patent prosecution history of U.S. Appl. No. 12/588,306, filed Oct. 9, 2009, entitled, "Open Platform Hybrid Manual-Automated Sample Processing System," now U.S. Pat. No. 8,703,492, issued Apr. 22, 2014.
Entire patent prosecution history of U.S. Appl. No. 12/617,485, filed Nov. 12, 2009, entitled, "Sample Rack System," now U.S. Pat. No. 8,142,740, issued Mar. 27, 2012.
Entire patent prosecution history of U.S. Appl. No. 14/229,156, filed Mar. 28, 2014, entitled, "Open Platform Automated Sample Processing System."
International Search Report for PCT Application No. PCT/US07/66177 date of completion Sep. 4, 2007, dated Sep. 25, 2007.
Office Action for Taiwan Patent Application No. 98138422 dated May 9, 2014, including translation of search report.
Written Opinion of the International Searching Authority for PCT Application No. PCT/US07/66177, date of completion Sep. 12, 2007.
Examination Report for Australia Patent Application No. 2009347207 dated Dec. 4, 2013.
Office Action for U.S. Appl. No. 12/588,306, filed Oct. 8, 2009, dated Apr. 24, 24, 2013.
Office Action for U.S. Appl. No. 12/588,304, filed Oct. 9, 2009, dated Mar. 22, 2011.
Final Rejection for U.S. Appl. No. 12/588,304, filed Oct. 9, 2009, dated Nov. 17, 2011.
Office Action for U.S. Appl. No. 12/588,304, filed Oct. 9, 2009, dated Feb. 22, 2012.
Office Action for U.S. Appl. No. 12/617,485, filed Nov. 12, 2009, dated Dec. 22, 2010.
Office Action for U.S. Appl. No. 12/617,485, filed Nov. 12, 2009, dated May 13, 2011.
First Office Action for CN 200780053086.2 with English translation, State Intellectual Property Office of the People's Republic of China, dated Dec. 19, 2012.
Office Action for U.S. Appl. No. 12/588,306, filed Oct. 8, 2009, dated Nov. 29, 2012.
Curt Malloy, et al., "HPV DNA Testing: Technical and Programmatic Issues for Cervical Cancer Prevention in Low-Resource Settings," Alliance for Cervical Prevention; Dec. 2000; 27 pages.
PCT International Search Report for PCT/US2010/57262 dated Feb. 2, 2011; 2 pages.
PCT Written Opinion of the International Searching Authority for PCT/US2010/57262 dated Feb. 2, 2011; 7 pages.

\* cited by examiner

Sample Location Report

Customer Education
QIAGEN Gaithersburg
1201 Clopper RD
Gaithersburg, MD 20878

Status: Accepted
11/20/2008 8:18 AM

| Rack ID | Position ID | Sample ID | Patient ID | Date & time |
|---------|-------------|-----------|------------|-------------|
| 234 | 1A | 34547687908764435 | | 19 Nov, 9:12 AM |
| 123 | 2A | 43234567878987543 | | 19 Nov, 3:12 PM |
| 123 | 3A | 34547687908760234 | | 19 Nov, 4:12 PM |
| 123 | 4A | 43234567878987543 | | 19 Nov, 9:12 AM |
| 432 | 1B | 34547687908760854 | | 19 Nov, 9:12 AM |
| 432 | 2B | 43234567878987345 | | 19 Nov, 9:12 AM |
| 555 | 3B | 43234567878987345 | | 19 Nov, 3:12 PM |
| 555 | 4B | 43234567878987543 | | 19 Nov, 4:12 PM |
| 555 | 1C | 34547687908760854 | | 19 Nov, 9:12 AM |

Fig. 24

LABORATORY CENTRAL CONTROL UNIT METHOD AND SYSTEM

CROSS-REFERENCE TO RELATED APPLICATIONS

This application is a continuation of U.S. patent application Ser. No. 12/949,503, which was filed on Nov. 15, 2010, issued as U.S. Pat. No. 9,953,141 on Apr. 24, 2018, and claims the benefit of U.S. Provisional Patent Application No. 61/262,497, which was filed on Nov. 18,2009, all of which are hereby incorporated by reference m their entirety.

BACKGROUND

1. Field of the Art

The present disclosure relates to control of and coordination between automated sample processing systems, and provides systems and methods that permit the coordination of data flow between high-throughput specimen processing systems. Systems according to embodiments may track samples being processed in a plurality of systems including, but not limited to, pre-analytical systems, analytical systems, and Laboratory Information Systems (LISs). The coordination of data between a plurality of systems may provide tracking of samples across a plurality of systems and may provide remote monitoring of a plurality of instruments, samples, and testing materials. Aspects of the disclosed systems may be used independently or in other systems. In exemplary embodiments these central control units (CCU's) are used in conjunction with and to control parameters in automated high throughput systems for detecting proteins or nucleic acids or pathogens in clinical samples, especially viruses and bacteria such as HPV and Chlamydia. In some embodiments these CCU's may regulate high throughput systems that include nucleic acid amplification reactions.

BRIEF DESCRIPTION OF THE DRAWINGS

FIG. 16 depicts a user interface for viewing a sample location report, according to an embodiment.

FIG. 19 depicts a user interface for releasing samples from a worklist for genotyping, according to an embodiment.

FIG. 22 depicts a user interface for a plate map highlighting samples selected for reflex testing, according to an embodiment.

FIG. 24 depicts a user interface for sample location reporting for reflex samples, according to an embodiment.

DETAILED DESCRIPTION

Figure 1:
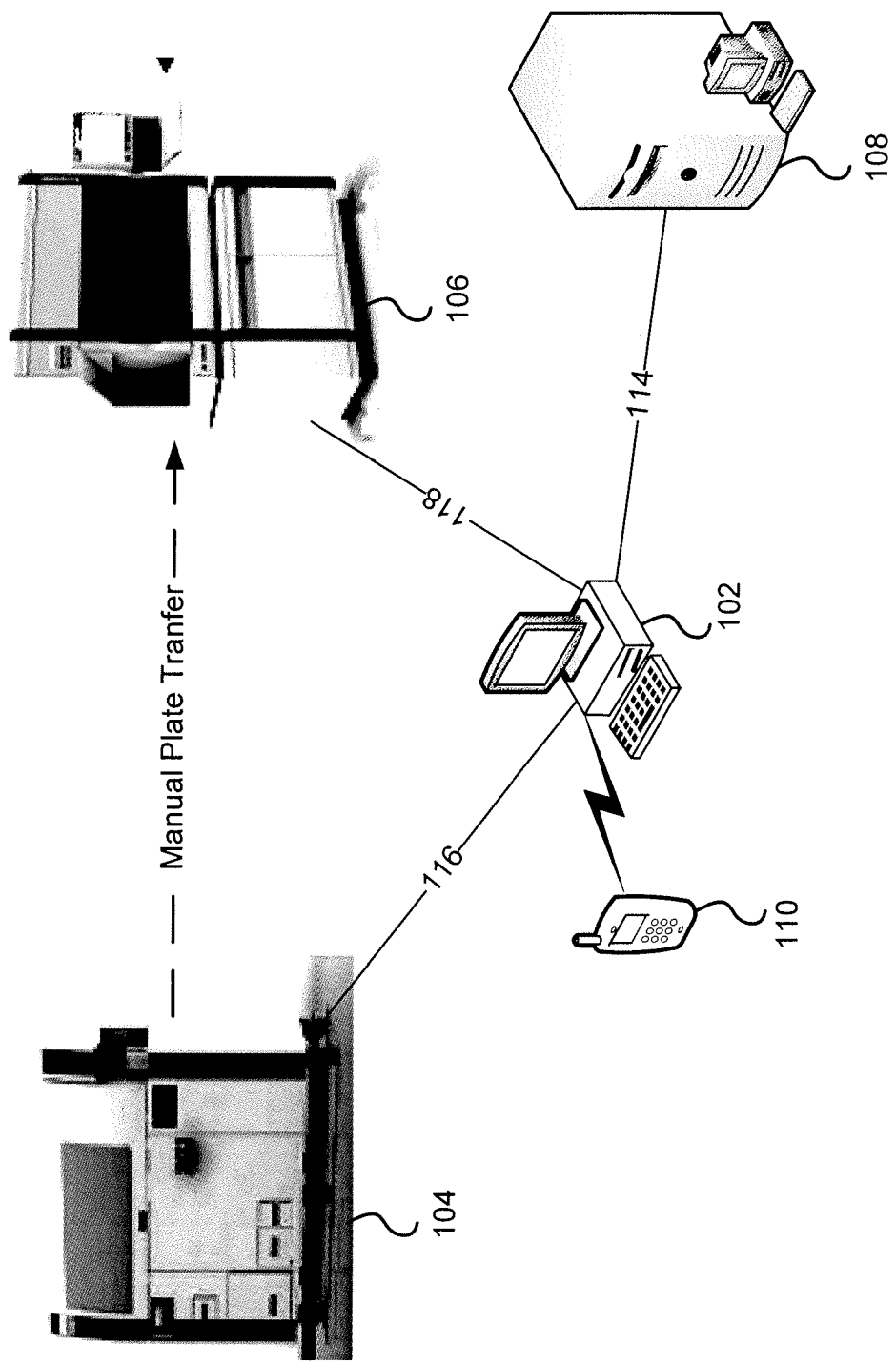
FIG. 1 depicts a system for control of and coordination between automated sample processing systems, according to one embodiment.

The present disclosure provides various exemplary embodiments of systems for control of and coordination between automated sample processing systems, Laboratory Information Systems ("LISs"), and other systems, as well as methods that permit the coordination of data flow between high-throughput specimen processing systems. Systems according to embodiments may use a Central Control Unit ("CCD") to track samples being processed in a plurality of systems including, but not limited to, pre-analytical systems, analytical systems, and Laboratory Information Systems ("LISs"). The coordination of data between a plurality of systems may provide data communication and testing coordination across systems and may provide remote monitoring of a plurality of instruments, samples, and testing materials.

Exemplary pre-analytical and analytical systems and assay methods that can be used for detection of HPV, CT/GC, cancer markers, or other constituents of clinical samples are described in: U.S. patent application Ser. No. 12/062,950, filed Apr. 4,2008; U.S. Provisional Patent Application Ser. No. 60/910,565 filed Apr. 6, 2007; U.S. Provisional Patent Application Ser. No. 61/113,855, filed Nov. 12, 2008; U.S. Provisional Patent Application Ser. No. 61/122,621, filed Dec. 15, 2008; U.S. Provisional Patent Application Ser. No. 61/185,081, filed Jun. 8,2009, entitled "Automated Human Papillomavirus Assay and System"; U.S. Provisional Patent Application Ser. No. 61/242,671, filed Sep. 15,2009; U.S. patent application Ser. No. 12/855,306, filed Oct. 9, 2009, entitled "OPEN PLATFORM AUTOMATED SAMPLE PROCESSING SYSTEM"; U.S. patent application Ser. No. 12/855,304, filed Oct. 9, 2009, entitled "AUTOMATED ASSAY AND SYSTEM"; U.S. Provisional Application Ser. No. 61/045,952, filed Apr. 17, 2008, entitled "COMPOSITIONS, METHODS, AND KITS FOR DETERMINING NUCLEIC ACID"; U.S. Provisional Application Ser. No. 61/113,841, filed Nov. 12, 2008, entitled "COMPOSITIONS, METHODS, AND KITS FOR DETERMINING NUCLEIC ACID,"; U.S. Provisional Application Ser. No. 61/231,371, filed Aug. 5, 2009, entitled "METHODS AND KITS FOR ISOLATING NUCLEIC ACIDS USING AN ANION EXCHANGE MATRIX"; U.S. Provisional Application Ser. No. 61/147,862, filed Jan. 28, 2009, entitled "SEQUENCE SPECIFIC LARGE VOLUME SAMPLE PREP SOLUTION UTILIZING HYBRID CAPTURE TECHNOLOGY,"; 61/147,623, filed Jan. 27, 2009, entitled "ISOTHERMAL HELICASE DEPENDENT MULTIPLEX ASSAY FOR DETECTION OF CHLAMYDIA TRACHOMATIS AND NEISSERIA GONORRHOEAE WITH FLUORESCENCE ENDPOINT DETECTION,"; U.S. Ser. No. 12/426,076, filed Apr. 17, 2009; U.S. Provisional Application Ser. No. 61/108,687, filed Oct. 27, 2008, entitled "NOVEL EAST RESULTS HYBRID CAPTURE ASSAY"; 61/179,848, filed May 1, 2009, entitled "NOVEL FAST RESULTS HYBRID CAPTURE ASSAY"; U.S. patent application Ser. No. 12/605,540, filed Oct. 26, 2009, entitled "Fast Results Hybrid Capture Assay and System"; Ser. No. 12/605,605, filed Oct. 26, 2009, entitled "Fast Results Hybrid Capture Assay On An Automated Platform"; U.S. Pat. No. 6,228,578, U.S. Provisional Application No. 61/180,821, U.S. Provisional Application No. 61/147,623; Tong et al., "Development of isothermal TaqMan assays for detection of biothreat organisms," BioTechniques Vol. 45, 543-557 (2008); Motré et al. "Enhancing helicase-dependent amplification by fusing the helicase with the DNA polymerase," Gene Vol. 420, 17-22 (2008); Chow et al., "Application of Isothermal Helicase-Dependent Amplification with a disposable Detection Device in a Simple Sensitive Stool Test for Toxigenic *Clostridium difficile,"* J. Mol. Diagnostics Vol. 10 (5), 452-458 (2008); Li et al., "Primase-based whole genome amplification," Nucleic Acids Research 36(13): e79 (2008); Goldmeyer et al., "Identification of *Staphylococcus aureus* and Determination of Methicillin Resistance Directly from Positive Blood Cultures by isothermal Amplification and Disposable Detection Device," J. Clin. Microbiol Vol. 46, 1534-1536 (2008); Kong et al., "New isothermal molecular diagnostic platforms," IVD Technology November issue (2007); Goldmeyer et al., "Development of a novel one-tube isothermal RT-tHDA platform for rapid RNA detection," J. Mol. Diagnostics Vol. 9, 639-644. (2007); Xu et al., "Simultaneous amplification and screening of whole plasmids using the T7 bacteriophage replisome," NAR 34(13): e98 (2006); An et al., "Characterization of a Thermostable UvrD Helicase and its Participation in Helicase Dependent Amplification," The Journal of Biological Chemistry Vol. 280, 28952-28958 (2005); and Vincent et al., "Helicase Dependent Isothermal DNA Amplification," EMBO reports Vol. 5, 795-800 (2004), the contests of each of which is incorporated by reference herein.

The systems described herein can be used to monitor and manage systems performing steps required in many common clinical or research laboratory methods. Exemplary embodiments monitor systems which can be used with a DNA analysis assay, such as the Digene HPV eHC test by QIAGEN Gaithersburg, Inc, in Gaithersburg, Md. ("Qiagen"). Other monitored systems may utilize the Next Generation Hybrid Capture® High Risk assay developed by QIAGEN Gaithersburg, Inc, in Gaithersburg, Md. ("Qiagen"). This assay may maintains high clinical sensitivity for high grade cervical disease established by the Hybrid Capture 2 during numerous large scale clinical studies, while creating a highly specific result. Examples of this and other assays that can be coordinated by embodiments of the systems described herein are disclosed in U.S. application Ser. No. 12/588,306, filed Oct. 9, 2009, entitled "OPEN PLATFORM AUTOMATED SAMPLE PROCESSING SYSTEM"; U.S. application Ser. No. 12/605,540, filed Oct. 26, 2009, entitled "FAST RESULTS HYBRID CAPTURE ASSAY AND SYSTEM"; "U.S. application Ser. No. 12/605,605, filed Oct. 26, 2009, entitled "FAST RESULTS HYBRID CAPTURE ASSAY ON AN AUTOMATED PLATFORM"; and U.S. Provisional Applications 61/108,687 filed Oct. 27, 2008; U.S. Provisional Application 61/174,848 filed on May 1, 2009; the contents of all of which are incorporated herein by reference in their entireties.

It will be understood that the foregoing assays are exemplary and that the present system may be used for managing and coordinating data between systems performing other clinical processes or detecting other moieties such as other nucleic acids, proteins, small molecules, cells, viruses, bacteria, fungi, yeast, mycoplasma and the like. Embodiments described herein may be adapted to provide the ability to manage and coordinate between systems performing a diverse set of common laboratory operations in a standard tube or plate format, with different systems readily constructed from combinations of processing stations to perform steps required in virtually any protocol. In some embodiments the CCU may be used to control parameters of automated systems feat allow for the detection of analyses which may be comprised in plates and/or tubes thereby providing for greater flexibility.

The CCU may connect and interface instruments (pre-analytical, analytical) and transfer load lists between the devices. The CCU may facilitate a high through-put automated diagnostic platform designed in the format of a laboratory system. It may serve as the data portal and mediator of data flow in this configuration and may have the capacity to connect the system to the LIS. The CCU may support tracking and treading of controls, perform result interpretation using raw data originating from the analytical instrument and report and print results generated by the analytical instrument.

According to some embodiments, the CCU may accept Manual Pre-analytical Chemistry (MPAC) input from a user. The CCU may provide a user interface for accepting user created plate maps and other data associated with manually created samples. As described in greater detail in reference to FIG. 4 below, the CCU may receive input via barcode readers and other interfaces. The CCU may allow manually created samples to then be transferred to an analytical system for processing.

The CCU may serve as a central hub of a high through-put automated diagnostic platform. According to some embodiments, the CCU may be responsible for the following: primary data repository for a high through-put automated diagnostic platform; remote monitoring of a high through-put automated diagnostic platform system status; management of dataflow between the instruments in a high through-put automated diagnostic platform; maintaining traceability for one or more samples, reagents, and other materials used on the system; maintaining adequate inventory control of samples, reagents and other materials used on the system; performance of data reduction to determine reportable results for one or more specimens am on the system; releasing results (e.g., to printed reports or to an LIS); and test order management for reflex testing to a genotype test.

Referring now to FIG. 1, an exemplary embodiment of a Central Control Unit is described in detail. FIG. 1 depicts a system for control of and coordination between automated sample processing systems, according to an embodiment. Central control unit ("CCU") 102 may be a PC containing controller software which may be communicatively coupled to a plurality of processing systems such as, for example, pre-analytic system ("PAS") 104 and analytical system ("AS") 106. CCU 102 may also be communicatively coupled to other systems such as Laboratory information system 108 and wireless communication device 110.

The PAS 104 or other embodiments of a pre-analytic system may be used in conjunction with an analytical system that analyzes or tests the samples (such as by analyzing DNA that may be present in the sample). For example, analytical system 106 may be an analytical system may be capable of carrying out the steps of a nucleic acid detection assay such as those described in Qiagen's Hybrid Capture 2 assay or QIAensemble assay protocols. Such steps may include sample loading, target nucleic acid denaturation, probe hybridization, target capture, signal production, signal detection and assay result reporting. An exemplary analytical system that may be used to perform these or other assays is the QIAensemble 2000, available from Qiagen.

The exemplary PAS 104 may be a generally self-contained unit having various input and output locations at which an operator can provide supplies and remove waste and processed samples. In the exemplary embodiment, the PAS 104 may include a sample rack input, a sample rack output, a control vial and reject vial access point, a first pipette tip input, an ETU input, reagent trays, a second pipette tip input, a sample plate input, a sample plate output, and one or more solid waste outputs. PAS 104 may be adapted to process biological samples, including liquid-cased cytology (LBC) samples into standard 96-well plates containing the extracted sample nucleic acid. During processing, the samples may be taken from standard sample containers, and processed in a strip of test tubes, called the extraction tube unit ("ETU"). According to some embodiments, 384 well plates may be used.

Central control unit (CCU) 102 may be used to control and/or monitor the PAS 104 and/or a downstream analytical system, and an exemplary CCU may provide a processing interface between the PAS and the analytical system. For example, a CCU may be combined with a PAS and an analytical system to perform all of the steps necessary to pre-process and test a sample according to the Hybrid Capture 2 or QIAEnsemble assay protocols.

The CCU and other interfaced systems (e.g., PAS 104 and AS 106) may designed to be used in a high volume laboratory. The CCU may be designed for use in a laboratory environment where exposure to chemical spills and other contaminations is possible. According to some embodiments, the CCU and other interfaced systems (e.g., PAS 104 and AS 106) may designed to be used by trained laboratory technicians. Help files may be provided on the CCU to provide on-screen support in order to resolve questions that a trained operator might have. In addition, approved labeling may also be provided to answer questions that may arise during use of the CCU and/or interfaced systems. Although illustrated as connected to a single PAS and a single AS, according to some embodiments CCU 102 may support a plurality of PAS and a plurality of AS (e.g., four PAS and four AS systems). According to some embodiments, CCU 102 may accept manually created samples and may allow transfer of manually created plates to an AS for processing.

CCU 102 may be a desktop computer, a laptop computer, a server, or other computer. According to some embodiments, CCU 102 may have a number of features facilitating use in a laboratory environment. CCU 102 may have a touch screen that may be used by an operator wearing gloves. CCU 102 may have a sealed keyboard that may be used in a laboratory environment by an operator wearing gloves. CCU 102 may be capable of running one or more operating systems (e.g., Microsoft Windows Vista for Embedded Systems, Microsoft Windows Vista, Mac OS X, Linux, etc.). Exemplary specifications of CCU 102 may include:

- a processor speed of 3 GHz;
- 4 GB of system memory;
- at least one 80 GB hard drive;
- at least one USB ("Universal Serial Bus") 2.0 or USB ("Universal Serial Bus") 3.0 Standard-A port;
- one or more components for producing audio output (e.g., internal speakers, external speakers, and a soundcard or integrated audio circuitry);
- at least one optical media drive capable of reading and writing CD-R, CD-RW, DVD-R, DVD-RW, DVD+R and DVD+RW disks;
- one or more network interfaces (e.g., a 100Base-T, 1000Base-T Ethernet interface); and
- advanced graphics capabilities (e.g., support for running DirectX 9 graphics with: a WDDM ("Windows Display Driver Model") Driver, 128 MB graphics memory, a Pixel Shader 2.0 supported in hardware, and support for 32 bits per pixel).

CCU 102 may also be equipped with one or more external devices such as, for example, a hand-held barcode reader, a keyboard (e.g., United States QWERTY keyboard or a US-International QWERTY keyboard); a display (e.g., a 17" touch screen monitor that supports a resolution of 1280× 1024 pixels.)

CCU 102 may be communicatively coupled to a network (e.g., an isolated 100Base-T or 1000BaseT Ethernet network dedicated to the CCU and interfaced systems) which may be used to connect CCU 102 to PAS 104 and AS 106 via network connections 116 and 118 respectively. According to some embodiments, this network may use TCP/IP. Additional systems or components may be connected to this network, including, but not limited to, additional PASs, additional analytical systems, and one or more printers. CCU 102 may have access to the printer which may be capable of printing reports, logs, and other documents originating from the CCU, an analytical instrument, and a pre-analytical instrument. Exemplary components of the network may include Ethernet hubs, Ethernet switches, one or more uninterruptible power supplies (UPS) (e.g., one or more UPS sufficient to power the network infrastructure for 15 minutes). According to some embodiments, only the Pro-Analytical Systems (PASs), Analytical Systems (AS), and the CCU may be connected to the network. Furthermore, the network may be the only data communication interface with the Pre-Analytical Systems (PASs) and the Analytical Systems (AS).

According to some embodiments, CCU communication with a PAS may include bi-directional communication for a range of activities including, but not limited to: startup, setup, processing, on-going communication, and data updates. For example, startup data may include registration of an instrument (e.g., a PAS), receipt of data (e.g., item container data, reagent container data, sample container data, well information, etc.). The CCU may also receive a test schedule from one or more Pre-Analytical Systems. The CCU may receive data during sample preparation execution and may update a data repository and one or more displays. Data received during sample preparation may include, but is not limited to: container location, sample status, reagent use, wash buffer data, waste container data, etc. Other data received by a CCU from a PAS may include bar code data which may indicate an item loaded into the AS.

According to one or more embodiments, a CCU may receive or provide one or more inputs via a user interface or communicatively coupled devices. For example, a user interface of the CCU may includes but is not limited to, login of one or more users, reporting, viewing of instrument(s) status, viewing of a work list, viewing of test results, and user/operator management.

According to some embodiments, CCU communication with an AS may include bi-directional communication for a range of activities including, but not limited to: startup, setup, processing, on-going communication, and data updates. For example, startup data may include registration of an instrument (e.g., an AS), receipt of data (e.g., item container data, reagent container data, sample container data, well information, etc.). The CCU may also receive a test schedule from one or more Analytical Systems. The CCU may receive dale, during sample preparation execution and may update a data repository and one or mom displays. Data received during sample preparation may include, but is not limited to: container location, sample status, reagent use, wash buffer data, waste container data, etc. Other data received by a CCU from an AS may include bar code data which may indicate an item loaded into the AS.

According to some embodiments, CCU 102 may also be connected to LIS 108 via network connection 114. Network connection 114 may use a variety of protocols including, but not limited to, a health level 7 (HL7) based interface, or an American Society for Testing and Materials (ASTM) based interface. CCU 102 may receive one or more work orders and other data from LIS 108 via network connection 114. CCU 102 may also provide data such as test results to LIS 108. As described in greater detail below. CCU 102 may analyze test results prior to providing test results via LIS 108, via a report or a display.

According to some embodiments, CCU 102 may communicate with other systems. For example, a CCU may determine that one or more consumable materials used for testing such as, for example, pipette tips, reagents, wash buffer, sample plates, and ETUs are getting low. CCU 102 may interface with an inventory or supply chain management system for ordering or restocking supplies. Such an interface may be to an internal system or may provide order information to a vendor based system.

In addition to reports and a user interface of CCU 102, CCU 102 may provide notification to users via email, a SMS (Short Message Service) communication, a text message, a phone call, a page, or by other electronic communications. Notifications may be configured by an authorized user to reach the user via a specified electronic address for one or more events. For example, an operator of CCU 102 may provide a phone number associated with wireless communication device 110 to receive alerts associated with the processing of one or more sets of samples. An alert may occur if a consumable level is running low and needs restocking if a waste container is reaching capacity, if an error code has been received from PAS 104, AS 106, or CCD 102, or if a process has completed. An operator monitoring CCU 102 may also receive a notification if an order has been received from LIS 108. The events that prompt notifications, notification contact information (e.g., a phone number, m email address), and notification contact methods (e.g., phone call, email, fax, page, SMS message, text message) may be configurable.

According to some embodiments CCU 102 may provide remote diagnostic information to one or more systems. Remote diagnostic information may include error codes and other data received from a PAS, an AS, or another instrument. Remote diagnostic information may also include calibration information for one or more instruments, results, and statistics associated with results. For example, carryover may be assessed by measuring the RLU (Relative Light Unit)/CO (Cutoff) of negative specimens that were processed just before and just after a high positive specimen. Other statistics may be analyzed such as, for example, a number of invalid test results for a population size and a number of positive samples for a population size. This information may be provided automatically by the CCU 102 or may be released by an operator of CCU 102 to a remote system. Other remote diagnostic information may be associated with error codes. Certain error codes and associated data may be provided to an external system by CCU 102. For example, if CCU 102 receives an error code indicating that a pipetting instrument of PAS 104 has encountered an error, CCU 102 may provide data associated with the error to aa external system. The external system may be a support system of a vendor. Data associated with the error may include dana indicating a current state of PAS 104 (e.g., a status of samples currently being processed including samples processed by a pipetter, the last calibration results of a pipetter, the serial number, bar code, manufacturer and other information associated with a pipetter, and a software version used by PAS 104). CCU 102 may produce one or more diagnostic or error reports to provide to m external support system.

According to one or more embodiments, a CCU may provide remote access to a diagnostic or support system. A CCU may implement audit tracking and otter security measures to verify integrity of data and operations. Remote access may be provided via a virtual private network or using other secure measures. Remote access may require an operator of a CCU or another authorized user to provide access. A CCU may also export one or more portions of data and provide them securely to a remote diagnostic and support team.

Remote diagnostic data provided by a CCU may provide as indication of a current or future service need. Remote diagnostic data may allow the scheduling of preventive maintenance based on received data. Analysis of diagnostic data provided from a plurality of CCUs may identify trends (e.g., maintenance periods) for one or more systems or instruments.

According to some embodiments, CCU 102 may receive information from an external system. Information may include diagnostic test information, troubleshooting information, software updates, and patches. Information received from an external system may be used by an operator of CCU 102 to troubleshoot one or more errors.

Of course, the CCU, or various parts of it, may be integrated into the PAS 104 itself, in which case the PAS 100 may be provided with a human interface to receive operating instructions and/or display system status. Such an interface may include various interface elements known in the art, such as a monitor, touch-screen monitor, keyboard, mouse, microphone, speaker, barcode reader, and so on. Similarly, one or more portions of the CCU may be integrated into AS 106, in which case AS 106 may provide access to CCU functionality via a human interface. While the shown arrangement of inputs and outputs has been selected for this embodiment, it will be understood that other arrangements may be used in other embodiments.

Figure 2:
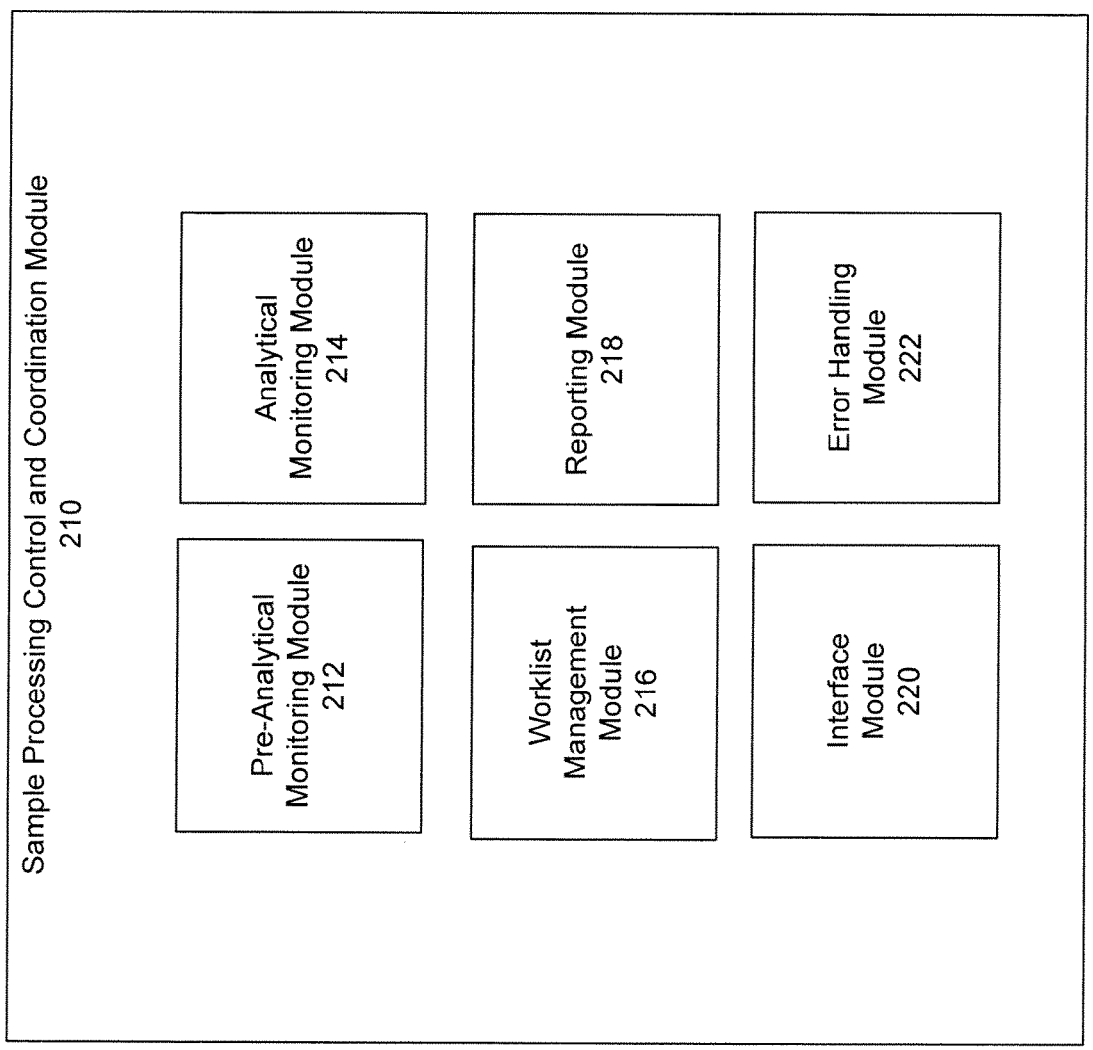
FIG. 2 shows a module for control of and coordination between automated sample processing systems, according to one embodiment.

FIG. 2 shows a module for control of and coordination between automated sample processing systems, according to an embodiment. As illustrated, sample processing control and coordination module 210 may contain one or more components including pre-analytical monitoring module 212, analytical monitoring module 214, worklist management module 216, reporting module 218, interface module 220, and error handling module 222.

The description below describes network elements, computers, and/or components of a system and method for portable device data archiving that may include one or more modules. As used herein, the term "module" may be understood to refer to computing software, firmware, hardware, and/or various combinations thereof. Modules, however, are not to be interpreted as software which is not implemented on hardware, firmware, or recorded on a processor readable recordable storage medium (i.e., modules are not software per se). It is noted that the modules are exemplary. The modules may be combined, integrated, separated, and/or duplicated to support various applications. Also, a function described herein as being performed at a particular module may be performed at one or more other modules and/or by one or more other devices instead of or in addition to the function performed at the particular module. Further, the modules may be implemented across multiple devices and/or other components local or remote to one another. Additionally, the modules may be moved from one device and added to another device, and/or may be included in both devices.

Pre-analytical monitoring module 212 may monitor one or more pre-analytical systems such as, for example, PAS 104. Pre-analytical monitoring module 212 may track sample processing by one or more pre-analytical systems. Pre-analytical monitoring module 212 may also track consumables such as, for example, pipette tips, reagents, wash buffer, sample plates, and ETUs. Tracked information may include information used to calculate an amount of one or more consumables required for scheduled sample processing (e.g., based on samples loaded for processing at a PAS.) Other tracked consumable information may include expiration information associated with consumable material, a shelf life of consumable material, and an opening date/time of container of consumable material (e.g., a reagent pack). Other information tracked by pre-analytical monitoring module 212 may include a remaining capacity of one or more waste containers. Pre-analytical monitoring module 212 may obtain data from a PAS which may be used to provide one or more interfaces, reports, and notifications on a CCU. Pre-analytical monitoring module 212 may also obtain diagnostic data, instrument data, and other status data. PAS data may be queried by pre-analytical monitoring module 212 or provided to pre-analytical monitoring module 212. According to some embodiments, pre-analytical monitoring module 212 may reside on a PAS and may transmit data to a CCU.

Analytical monitoring module 214 may monitor one or more analytical systems such as, for example, AS 106. Analytical monitoring module 214 may track sample processing by one or more analytical systems. Analytical monitoring module 214 may also track consumables such as, for example, trays, pipette tips, reagents, wash buffer, sample plates, and ETUs. Tracked information may include information used to calculate an amount of one or more consumables required for scheduled sample processing (e.g., based on samples loaded for processing al as AS.) Other tracked consumable information may include expiration information associated with consumable material, a shelf life of consumable material, and an opening date/time of container of consumable material (e.g., a reagent pack). Information tracked by analytical monitoring module 214 may include, but is not limited to, a remaining capacity of one or more waste containers. Analytical monitoring module 214 may obtain data from an AS which may be used to provide one or more interfaces, reports, and notifications on a CCU. Analytical monitoring module 214 may also obtain diagnostic data, instrument data, and other status data. AS data may be queried by analytical monitoring module 214 or provided to analytical monitoring module 214. According to some embodiments, analytical monitoring module 214 may reside on an AS and may transmit data to a CCU.

Worklist management module 216 may track samples and provide data indicating a status of samples on a pre-analytical system, a status of samples on m analytical system, a indication of results, a mapping of samples on a sample plate, and other sample management data. Worklist management module 216 may provide the tracking of a sample from receipt of a work order, pro-analytical processing, analytical processing, results analysis, and release of results.

Reporting module 218 may provide one or more user interfaces and reports. Reports may include, but are not limited to: an individual patient report; a results report; a plate map report; an assay report; a reagent report; a controls report; and a sample location report.

Interface module 220 may provide interfaces to one or more external systems. External systems Bay include, but are not limited to, an LIS, an online inventory system, and a supply chain management system.

According to one or more embodiments, a CCU may provide remote access to a diagnostic or support system. A CCU may implement audit tracking and other security measures to verify integrity of data and operations. Remote access may be provided via a virtual private network or using other secure measures. Remote access may require an operator of a CCU or another authorized user to provide access. A CCU may also export one or more portions of data and provide them securely to a remote diagnostic and support team.

Remote diagnostic data provided by a CCU may provide an indication of a current or future service need. Remote diagnostic data may allow the scheduling of preventive maintenance based on received data. Analysis of diagnostic data provided from a plurality of CCUs may identify trends (e.g., maintenance periods) for one or more systems or instruments.

Error handling module 222 may handle one or more errors received from a pre-analytical system, an analytical system, a CCU, or another connected instrument or system. Error handling module 222 may handle one or more errors encountered with an interface to an external system. According to some embodiments, error handling module 222 may provide notifications of errors via reporting module 218. Error handling module 222 may also provide notification to users via email, a SMS (Short Message Service) communication, a text message, a phone call, a page, or by other electronic communications. Notifications may be configured by an authorized user to reach the user via a specified electronic address for one or more events.

Figure 3:
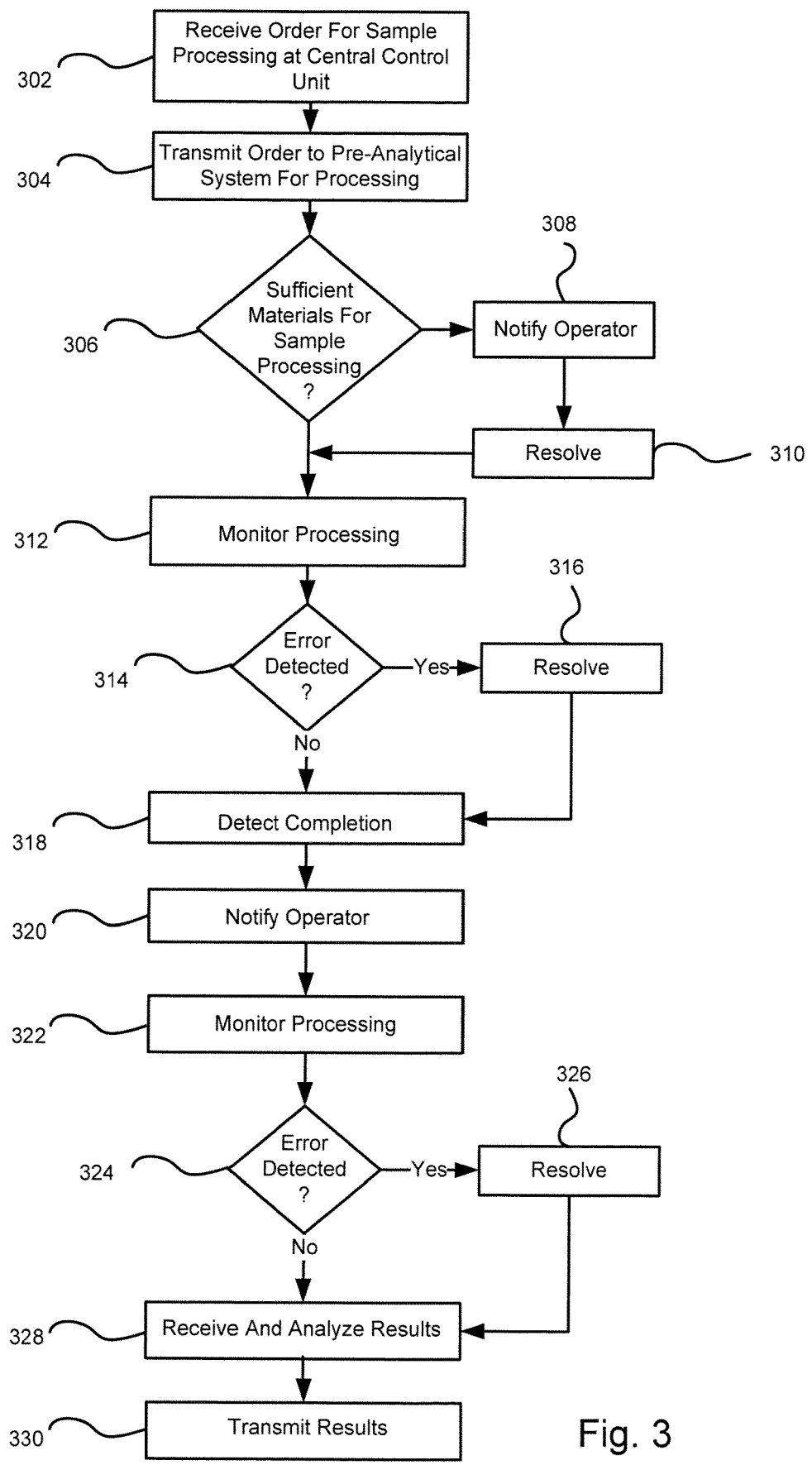
FIG. 3 depicts a method for control of and coordination between automated sample processing systems, according to one embodiment.

FIG. 3 depicts a method For control of and coordination between automated sample processing systems, according to an embodiment. At block 302, the method 300 for control of and coordination between automated sample processing systems may receive one or more orders for sample processing at a central control unit. For example, orders may be received at a CCU from a LIS or another external system. An operator may also enter orders. According to some embodiments, order information may include a requested test id, test name, or test protocol for one or more samples. Additional order information may include a sample id and patient information (e.g., a patient id, name, date of birth, address). Other order information may be received. According to some embodiments, a CCU receiving an order may automatically assign a test protocol to one or more samples associated with an order. In some embodiments, an operator at a CCU may assign a test protocol to one or more samples associated with an order.

At block 304, the method 300 may transmit one or more portions of an order to a pre-analytical system for processing. Transmitted information may include one or more sample ids, test protocol information, and other data that may be used by the analytical system for processing and tracking of samples.

The CCU may receive information about consumable materials used by the pre-analytical system for sample processing. For example, bar codes, RFID tags, or other identifiers may be placed on consumable materials such as reagent packs, pipette tips, wash buffer containers, sample plates. Analytical systems, pre-analytical systems, and other instruments may scan consumable materials as they axe loaded into the systems. This data may be provided to a CCU. Analytical systems, pre-analytical systems, and other instruments may track consumption of consumable materials and communicate this data to the CCU. At block 306, the CCU may determine whether there are sufficient materials on a pre-analytical system for processing the samples in the order. According to one embodiment, a CCU may contain data regarding the materials present on a system and the system (e.g., a pre-analytical system) may contain logic determining whether such materials are sufficient for processing. If a PAS contains sufficient materials for sample processing the method 300 may continue at block 312. If a PAS does not contain sufficient materials for sample processing, the method 300 may continue at block 308.

At block 308, one or more operators may be notified. According to some embodiments, an operator may be notified remotely (e.g., paged, sent an email, sent a text message, or sent a voicemail). A user interface associated with the CCU, an interface of the PAS, or interfaces of both systems may provide notifications (e.g., pop-up alerts on a screen) about required materials. According to some embodiments, a pre-analytical system may not begin processing a sample until sufficient materials are loaded for processing of the sample.

At block 310, an operator may resolve the issue by loading one or more consumable materials for the sample processing (e.g., loading a reagent pack). A user interface at the CCU may provide instructions on loading an appropriate consumable material which may include diagrams and click through steps. The pre-analytical system may detect the loading of the consumable material (e.g., by scanning a barcode on a package) and may provide the information to the CCU. Processing of one or more samples may begin. In some embodiments, an instrument such as a PAS may begin processing a first set of samples as soon as it receives them and loading of additional consumable materials for the remaining loaded samples may not interrupt the processing.

At block 312, the CCU may monitor processing. The CCU may receive data from a plurality of components of pre-analytical systems and analytical systems. The CCU may receive data associated with; automated pipetting subsystems or components of a PAS; incubators; supply containers (e.g., levels which may be monitored by sensors); luminometers, fluorometers; incubators; agitators, orbital shakers, actuators (e.g., an access arm or gripper used to transport samples), capping and decappiag units, and other instruments. The CCU may contain or receive one or more indicators of errors. For example, a CCU may receive an indicator of as error from a PAS (e.g., a pipettor drops a tip). A CCU may also process data to see if it meets specified criteria. Specified criteria may, by way of non-limiting example, include, a range. For example, a CCU may detect an error if an incubator is outside of a specified range. The specified criteria may vary depending on a test protocol of a sample currently being processed by an instrument (e.g., the acceptable temperature range for an incubator may vary by test protocol or the desired agitation period may vary by protocol). If an error is detected the method 300 may continue at block 316. If no errors are detected, the method may continue at block 318.

At block 316 the identified error may be resolved. Resolution may differ depending on the cause of the error. Resolution may result in one or more samples being marked as invalid (e.g., insufficient sample size). Resolution may involve continuing a process after a problem has been corrected.

At block 318, completion of one or more samples at the PAS may be detected. At block 320, an operator may be notified. As illustrated in FIG. 1, an operator may manually transfer one or more sample plates or other containers from a pre-analytical system to an analytical system. The analytical system may begin processing one or more samples. Prior to processing or during processing the CCU may determine whether the analytical system has sufficient materials for processing. According to one embodiments a CCU may contain data regarding the materials present on a system and the system (e.g., an analytical system) may contain logic determining whether such materials are sufficient for processing, the CCU and/or analytical system may provide one or more notifications regarding materials (e.g., reagents, wash buffers) depending on levels.

At block 322, the CCU may monitor processing. The CCU may receive data from the analytical system associated with one or more instruments. The CCU may receive an error notification or may identify an error from received data. The CCU may use one or more specified criteria to evaluate portions of the data received from the analytical system. For example, a CCU may determine whether an sample cell count is adequate based on a measurement of turbidity against one or more specified criteria. If an error is detected the method 300 may continue at block 326. If no error is detected, the method 300 may continue at block 328.

At block 326, the identified error may be resolved. Resolution may differ depending on the cause of the error. Resolution may result in one or more samples being marked as invalid (e.g., low cellularity). Resolution may involve continuing a process after a problem has been corrected.

At block 328 results may be received and analyzed. The CCU may perform a plurality of tests to verify the results.

At block 330, the results may be released. Release of the results may be through one or more reports and/or transmission of one or more portions of the results to a LIS. Additionally, release of results may enable an operator to schedule one or more samples for reflex testing.

Figure 4:
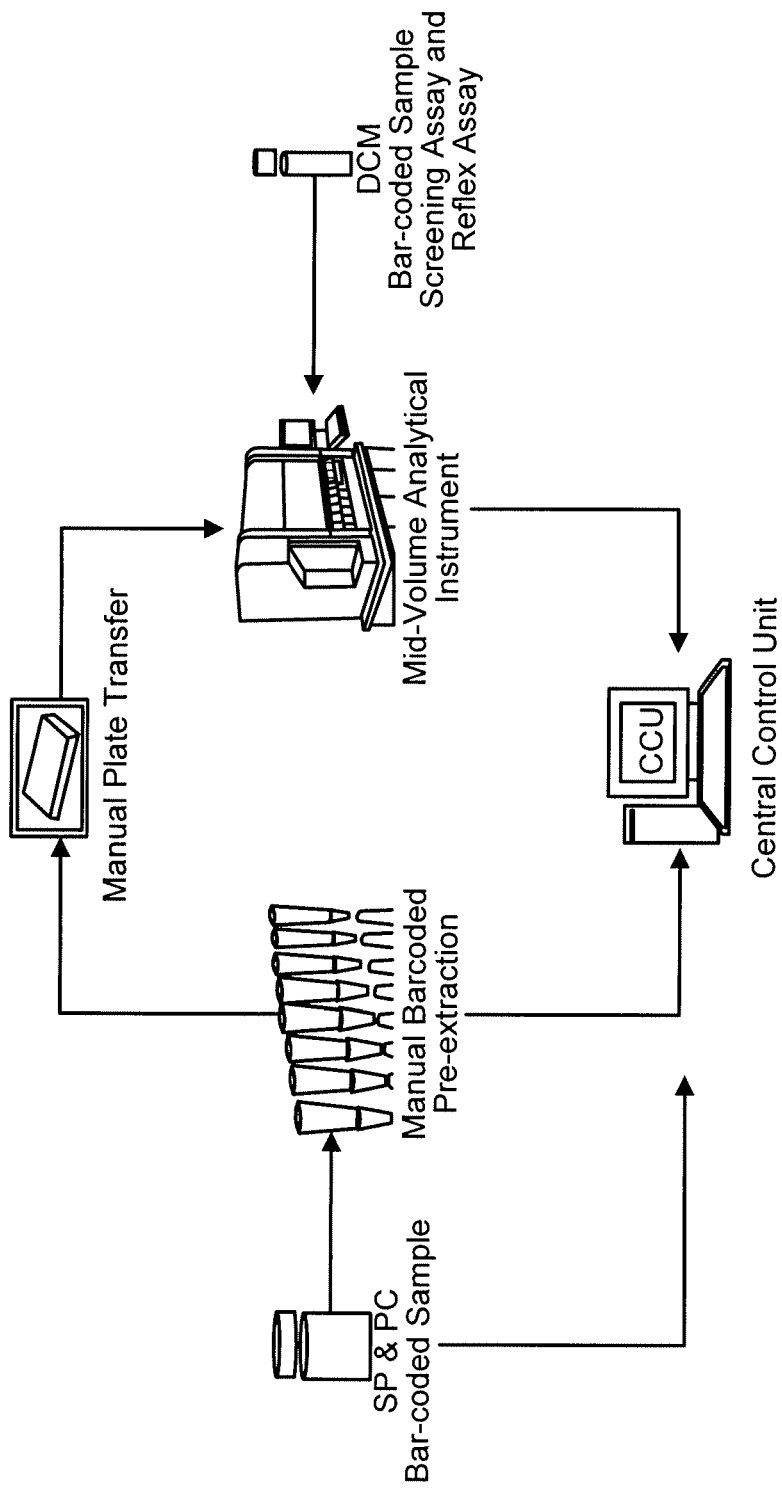
FIG. 4 depicts a system for acceptance of and control of manually created samples and automated analysis of such samples, according to an embodiment.

Referring now to FIG. 4, there is depicted a system for acceptance of and control of manually created samples and automated analysis of such samples. The manual pre-analytical chemistry (MPAC) process of the CCU may allow manual sample preparation of specimens to be entered and tracked (e.g., PreservCyt or Sure-Path specimens). The MPAC interface of the CCU may also allow a user to create plate maps in order for manually prepared samples to be transferred to plates for analysis by an AS. The MPAC interface may allow a user to add samples from manually prepared plates to a CCU Worklist As such, the MPAC components of the CCU may perform one or more the following: identifying sample tubes, extraction tubes, plates, and reagent kits used during MPAC; communicating sample tube, extraction tube, plate, plate map, and reagent kit information to the CCU; tracking sample location from sample tube to extraction tube to plate well; creating plate maps and transmitting plate maps to the CCU so that they may be processed by an AS.

The MPAC interface of the CCU may accept barcode entries, manually entered text, and other inputs. For example, a barcode reader communicatively coupled to the CPU may allow entry of plate barcodes, sample bar-codes, extraction tube identifiers, reagent kit barcodes, and other identifiers. Data manually entered via a keyboard may require confirmation (e.g., two entry fields may be provided to require a user to confirm a number. The MPAC interface of the CCU may allow a user to assign a test order to a sample barcode. The MPAC interface may also allow a user to update test progress associated with a sample (e.g., associate a sample with an extraction tube, add/remove samples to and from a worklist, and associate a well on a plate with a sample). The MPAC interface may provide several different views allowing a user to navigate information including views organized by sample, plate, worklist, supplies, etc.

The MPAC interface may enforce one or more rules. For example, a user may be required to have controls or calibrators on a plate before committing a plate map. The MPAC interface may enforce other rules (e.g., allowing a sample to occupy only one well per plate for HPV assays, ensuring that users cannot place samples into wells reserved for calibrators on the plate map, ensuring that users cannot place samples into unavailable wells on the plate map, allow samples associated with a test or tests to be placed only on a plate map associated with the same test or tests. According to some embodiments, the MPAC software may identify to the user, via a graphical UI, the next location where a sample should be placed.

Figure 5:
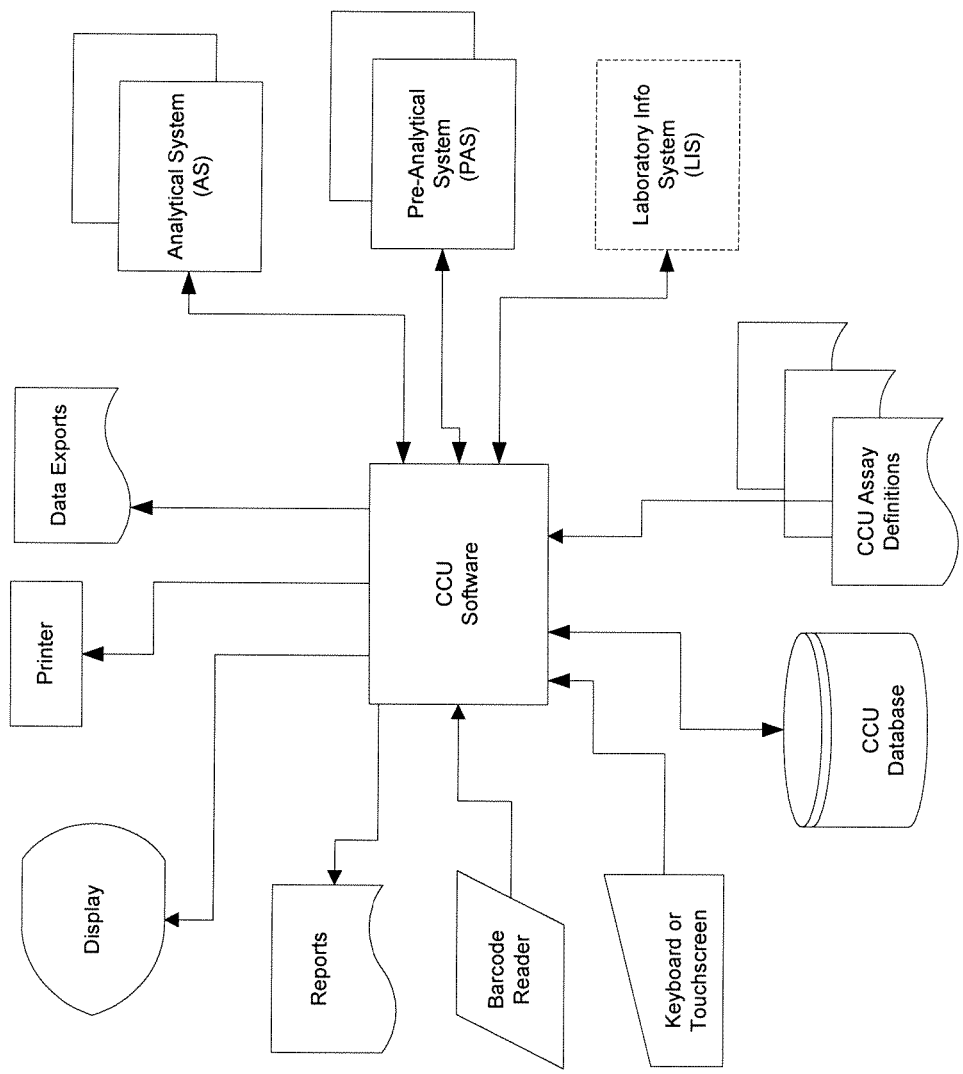
FIG. 5 is a diagram of exemplary inputs and outputs of a CCU, according to an embodiment.

An exemplary diagram of inputs and outputs of a CCU is depicted in FIG. 5. As illustrated in FIG. 5, a CCU may receive one or more assay definitions. An assay protocol may have an external object definition. Assay objects may be loosely coupled with a core CCU system. An assay versioning scheme may be pro vided by a CCU to associate results with the version of an assay used to create results. The CCU Assay Definitions input source may allow loading assay protocol definitions from an XML file in a way that allows new assay definitions to be deployed without software or database changes.

The CCU Database, AS, PAS, and LIS may be external systems to a CCU that may serve both as a source of input and as a target of output. The CCU architecture may be designed in a manner to hide specific hardware and software interface details of the AS and PAS, An instrument interface library component may be used for instrument communication so any instrument that can communicate through the instrument interface library can be integrated into a CCU system in the future.

The CCU system may provide integration with a variety of Laboratory Information Systems (LIS's) which may be installed at a customer's facility. Two exemplary LIS communication protocols that may be supported are ASTM 1381/1394 and HL7. ASTM 1394 and HL7 are data format standards, while ASTM 1381 is a low-level transport protocol standard that is used by ASTM 1394. The communication transport used for the HL7 protocol may be TCP/IP. While the protocols, transports, and command set for communicating between instruments and an LIS may be standardized flexibility may be built into an LIS interface in a CCU to accommodate either LIS vendor-specific data and behaviors, or customer site-specific requirements.

The interface between CCU and LIS may be a bidirectional interface. Use LIS-to-CCU direction may provide lab orders and patient data that needs to be translated into test runs on the instruments and the CCU-to-LIS direction may provide the communication of test results back to LIS and querying LIS for patient information for a sample being processed by the CCU.

Figure 6:
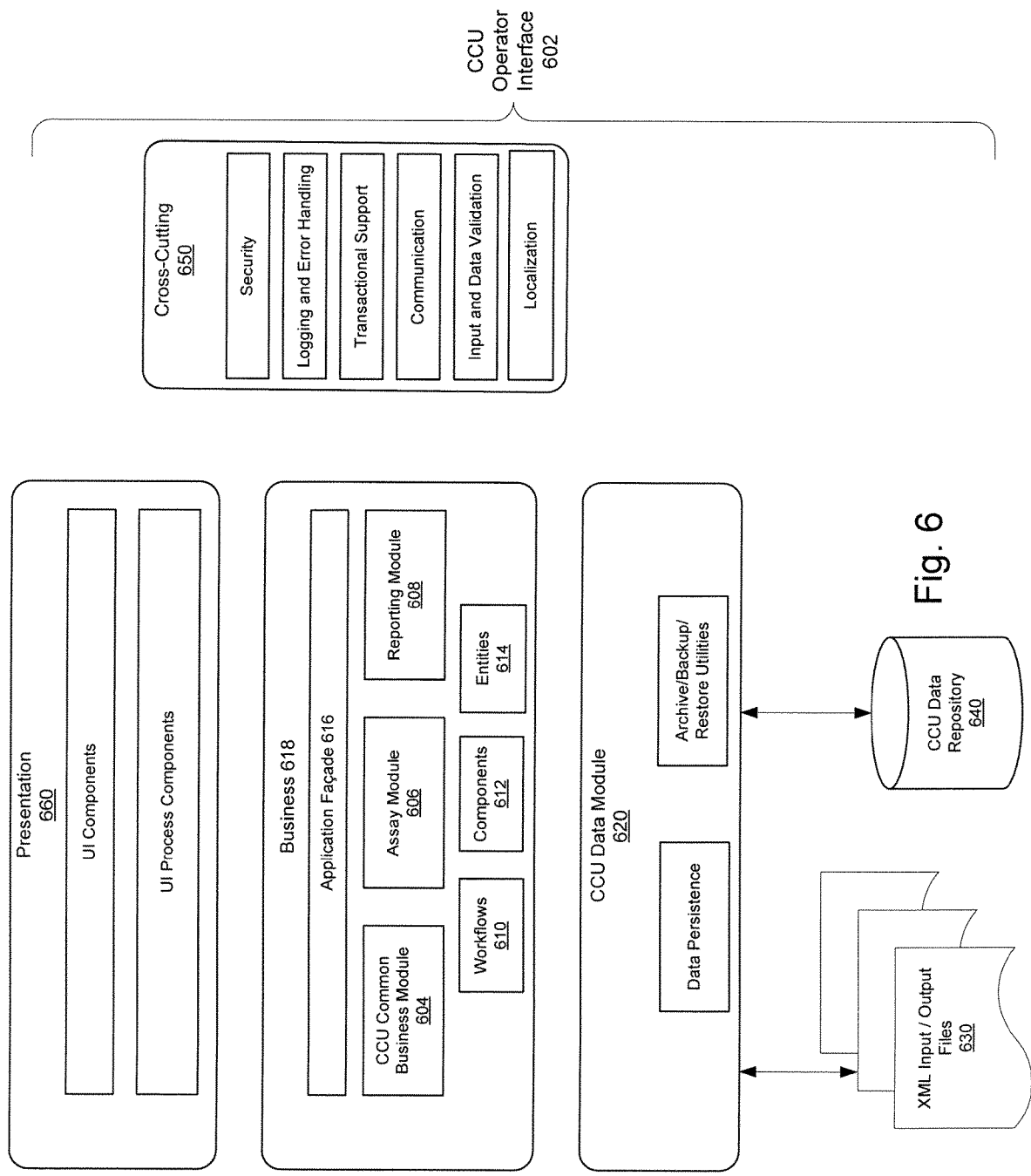
FIG. 6 is a diagram illustrating components of a CCU operator interface, according to an embodiment.
Figure 7:
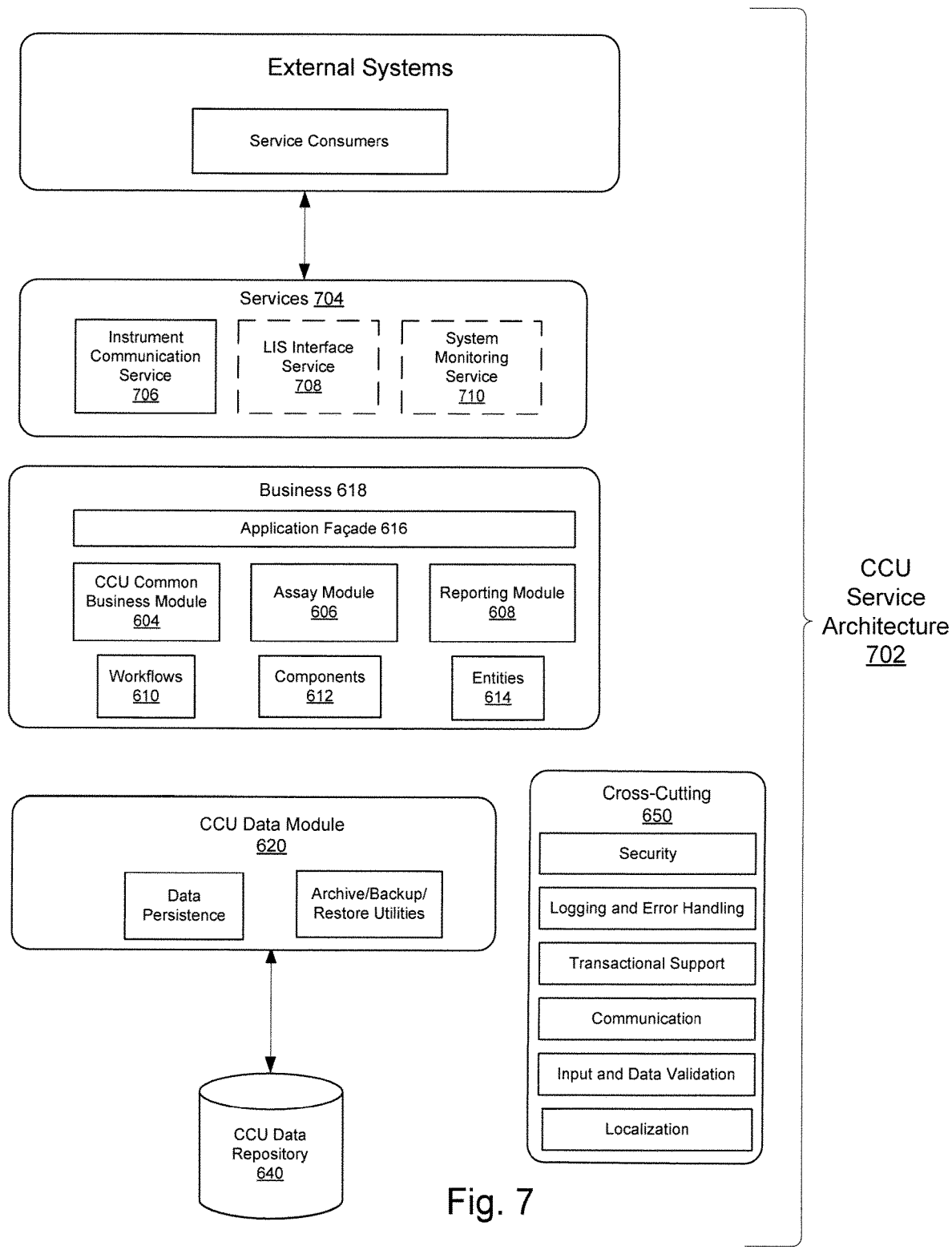
FIG. 7 is an exemplary graphical view of the logical composition of the major components of a CCU system, according to an embodiment.
Figure 8:
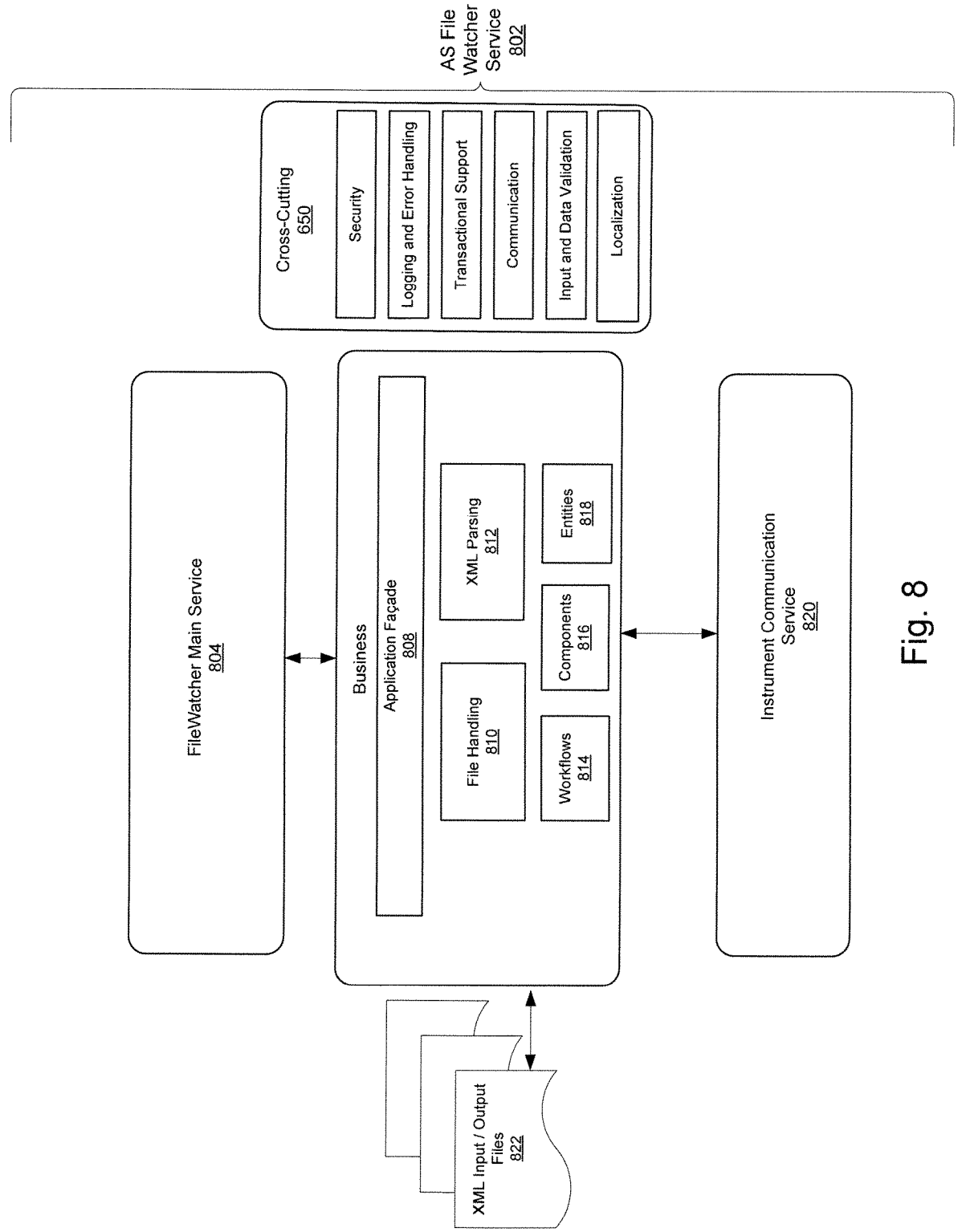
FIG. 8 is a diagram depicting components of a file watcher service, according to an embodiment.

Referring now to FIGS. 6-8, there is depicted an exemplary graphical view of the logical composition of the major components of a CCU system, based on exemplary high level components and common services. FIG. 6 illustrates components of a CCU operator interface. A CCU operator interface may be a primary user interface that a work ceil operator uses to view and manage data and workflow state within a CCU database. The CCU operator interface module may implements the primary operator user interface for a CCU system. Functionality implemented by a CCU Operator interface module may include, but are not limited to:

authentication of operators as they login to the CCU Operator Interface;

allowing operators with sufficient privileges to manage other operator accounts;

allowing operators to view the active work lists for each instrument in the work cell, where a work list entry may consists of a test protocol identifier, a sample identifier, current status of the test, and any events or comments associated with the work list entry;

allowing operators to view & reflex list of samples that have tested positive and may need to have a follow-up test run;

allowing operators to view status summary information for one or more instruments in the work cell, with status summary information consisting of test in progress, reagent and/or other supply status, connectivity of instrument;

allowing operators to run and print reports on completed and in-progress work on the instruments, including patient report, results report, plate map report, assay report, reagent report, controls report; and allowing operators to manage error and event information from the CCU and from each instrument in the work cell.

The CCU operator interface module of FIG. 6 may include other modules such as for example, a CCU Coalmen Business Module 604, an assay module 606, a reporting module 608, a workflows module 610, a components module 612, and an entities module 614.

Presentation module 660 may contain UI components and UI Process Components. UI components may include screen controls and logic that control the behavior of the control itself. UI Process Components may include larger groupings of screen controls and process flow and event passing between controls to manage a higher-level processing task.

According to some embodiments, the physical implementation of the CCU Operator interface and the physical implementation of these logical architectural components may follow a variation on the Model-View-Presenter (MVP) design pattern. The pattern followed may be Model-View-ViewModel (MVVM) and is a pattern that is based on Model-View-Presenter, but is tailored to take advantage of features in Windows Presentation Framework. Windows Presentation Framework (WPF) may be used for UI development framework for developer user interfaces in .Net and may be the user interface framework used to implement the CCU Operator Interface.

The MVVM pattern may take advantage of WPF's binding infrastructure. Properties of the View Model may be bound to graphical components of the View in a loosely coupled way and reduce or eliminate the traditional event handling and control updating logic that is involved with other frameworks. Use data binding system in WPF may also support automatic data input validation, further reducing coding requirements in the View layer and providing for standardized input validation error reporting.

Application façade 616 may be a mapping layer that converts data between the UI layer and the data storage layer, based on a typical differences in how data is structured for presentation versus how data is stored in a database or other repository.

A CCU Common Business Module 604 may be a business logic layer that may encapsulate data and behavior into objects usable by the UI and Services. For a CCU, exemplary candidate objects in this layer may be sample, Test Run, Patient, etc. A CCU Common Business Module 604 may implement a class library interface for one or more major business objects of the system. According to some embodiments, some modules may be separate (e.g., assay and reporting). Functionality implemented by this module may include, but is not limited to:

Encapsulation of behavior and data access/data storage for all major objects in the system, including: instruments, Instrument physical attributes (e.g., racks, trays, containers). Work lists, Samples, Patients, Test results, Sample containers (e.g., plates, tubes, ETUs, wells), Assay reagents, Events, and Operators;

Providing workflow operations across one or more business object components listed above;

Providing helper classes for communicating between a User Interface (UI) and a business module; and Providing domain objects for communicating with the data services layer for data storage.

The Assay Module 606 may incorporate assay loading from external files, assay version management, and data analysis of samples against assays. The Assay Module 606 may be a data reduction module that may implement a class library interface for assay and results calculation (data reduction). Exemplary functionality implemented by this module may include, but is not limited to:

Encapsulation of behavior and data access/data storage for one or more assay and test results calculation objects in a system, including: Assay, Assay configuration, Assay protocol, Calibration, Calibration parameters, Control. Control parameters, RLU limit parameters, and Data reduction parameters;

Providing workflow operations across one or mote business object components;

Providing helper classes for communicating between the UI and this business module;

Providing domain objects for communicating with the data services layer for data storage;

Dynamic loading of assay protocol definitions from XML files; and

Management of assay versioning and corresponding results versioning.

Reporting Module 608 may implement functionality for the definition of reports, the generation of reports from live data, and the printing and exporting of report data.

Reporting Module 608 may implement a class library interface for reporting services used by the user interface modules. Functionality implemented by this module may include, but is not limited to:

Providing a utility to define reports that may be executed by name and with parameters by higher level classes. Exemplary reports include: an Individual Patient Report; a Results Report; a Plate Map Report; an Assay Report; a Reagent Report; and a Controls Report;

Providing a user interface for accessing a list of available reports, specifying parameters for the reports, and managing the report result storage (e.g., on-screen, Excel, and PDF);

Providing classes to convert object-relational data (object graphs) to data sets for report generation; and Providing utility classes to support internationalization (e.g., strings, datetime, currency, printed page form factors).

CCU Data Module 620 may include object-data persistence for a CCU Common Business Module, data archival services, data purging, and backup and restoration functionality. CCU Data Module 620 may implement data persistence for domain objects from CCU Common Business Module 604, Assay Module 606, and Report Module 608 components. In addition, it may provide other database and file utilities and services. Functionality of this module may include:

Providing object persistence service that performs object-relational data mapping and save/restore of objects to/from a relational database;

Providing utility interfaces for data archiving and purging for use in GUI or console applications;

Providing utility interfaces for data backup and restore for use in GUI or console applications; and Providing utility classes for data serialization and mapping for class libraries and service programs.

Referring to FIG. 7, Instrument Communication Service 706 may include a command and response interface used by instruments to communicate with the CCU Common Business Services. According to some embodiments, Instrument Communication Service 706 may implement a Windows Service host interface and client library that may provide a communication interface used by instruments to communicate status to the CCU and to look up information from the CCU. This module may include a client library that may provide an interface that instruments bind to, providing flexibility for the actual service to be located on the local or a remote machine. Functionality provided by this module may include, but is not limited to:

Providing a class interface that may allow instruments to interact with the CCU Common Business module. The types of operations that instruments may perform with the class library may include: Instrument registration; Operator login; Sample container management; Reagent container management; and Event management.

Providing a Windows Service that may respond to requests from the instrument interface client library. The Windows Service services requests through use of the CCU Common Business module and Assay (Data Reduction) module.

LIS Interface Service 708 may implement a Windows Service and client library that may provide a bi-directional interface to customer LIS systems. This service may support both ASTM 1384/1391 and HL7 communication protocols for LIS communication as well as other protocols. Functionality provided by this module may include:

Supporting patient data streaming;
Supporting automatic run/sample results transmission;
Supporting manual ran/sample results transmission;
Supporting querying active database for patient data for given samples;
Supporting querying LIS host for patient data for given samples;
Supporting associating patient data to samples in the database, upon patient streaming or querying (LIS or database);
Supporting periodic patient data purge;
Supporting notification to the CCU Operator Interface of run packet transmission completion; and
Supporting notification to the CCU Operator Interface of LIS transmission connection status changes.

System Monitoring Service 710 may monitor the availability of key programs and services of the CCU system and alerting of operators if a key process or service is unavailable. System Monitoring Service 710 may implement a Windows Service host interface and corresponding monitoring agent programs that may monitor the "health" of program and service modules of the CCU system. Functionality provided by this module may include:

Providing a host interface that receives system monitoring events and routes events received to the CCU Common Business Module and Common Utility Concerns for logging and notification;
Providing monitoring agents that monitor specific services and program modules (File Watcher, Instrument Communication Service, CCU Database) and send events to the System Monitoring host service; and
Providing configurability of what monitored events trigger notification.

Monitored activities include, but are not limited to: (Process is alive; Process responding to heartbeat request; Events logged to event log that exceed configured warning thresholds; Database full; and Log file(s) full).

According to some embodiments, a CCU Remote Operator Interface may be provided. A CCU remote operator interface may provide access to one or more portions of functionality remotely and may be designed for a mobile client (e.g., an IPAD, a cell phone, a PDA, a laptop, etc.). A CCU remote operator interface may be accessible via a LAN (e.g., wireless access) to provide mobility within a worksite or remotely (e.g., via a secure VPN) to allow access to travelers.

Referring now to FIG. 8, XML Parsing 812 may translate between XML files and the Instrument Communication Services. This service process may run continuously on an AS machine to monitor and act on asynchronous file creation between a CCU and AS. XML Parsing 812 may implement a Windows Service that may read and write XML files that may be used to communicate directly with an AS instrument. (XML file-based communication may be a method of interacting with the AS instrument's control software.) Once an XML file is parsed and the request is understood, this service may use the Instrument Communication Services client library to interact with the CCU. Responsibilities of this module may include:

Translating XML file-based command requests coming from the AS Instrument into appropriate calls to the Instrument Communication Service module to send status and lookup requests from the AS to the CCU;
Creating XML files from responses received from the CCU to send results back to the AS;
Monitoring specified folders for new XML files generated from an AS machine and processing each file as it is found; and
Providing a recovery/retry service for files that fall to processed successfully.

As illustrated by the Cross-cutting module 650 of FIGS. 6-8, the following may be common services used by one or more other modules. Cross-cutting module 650 may be a class library of common utility concerns (also called "cross-cutting services") that may be used in one or more programs and services modules of the system. The specific major levels of functionality provided by this library may include: Security; Logging and Error Handling; Transaction Support; Communication; Input and Data Validation; and Localization.

Security may relate to protecting data and controlling access to the system. Encryption, user authentication, and checksum may be elements included in a Security module.

Logging and Error Handling may include a common method of logging errors and events, alerting operators of critical errors, and performing audit logging of operation and data access by operators. This module may be configurable in terms of what level of information is logged, what alerting methods are used, and what error log repositories are used.

A Transaction Support module may provide a common means of marking transaction boundaries and of committing or rolling hack transactions based on business logic and error detection in the business logic. This module may also be extended to cover object invalidation, which may occur if a transaction is rolled back.

A Communication module may provide general client/server conversational communication services (e.g., as supported by WCF or by lower-level interfaces like Sockets).

An input and Data Validation module may provide common validation services for use by a user interface and/or parsing layers. Common validations may consolidate code that may typically spread throughout the application and may often written redundantly and inconsistently.

A Localization module may provide services for returning an appropriate string, date, currency, sort order based on the locale of the operator.

Figure 9:
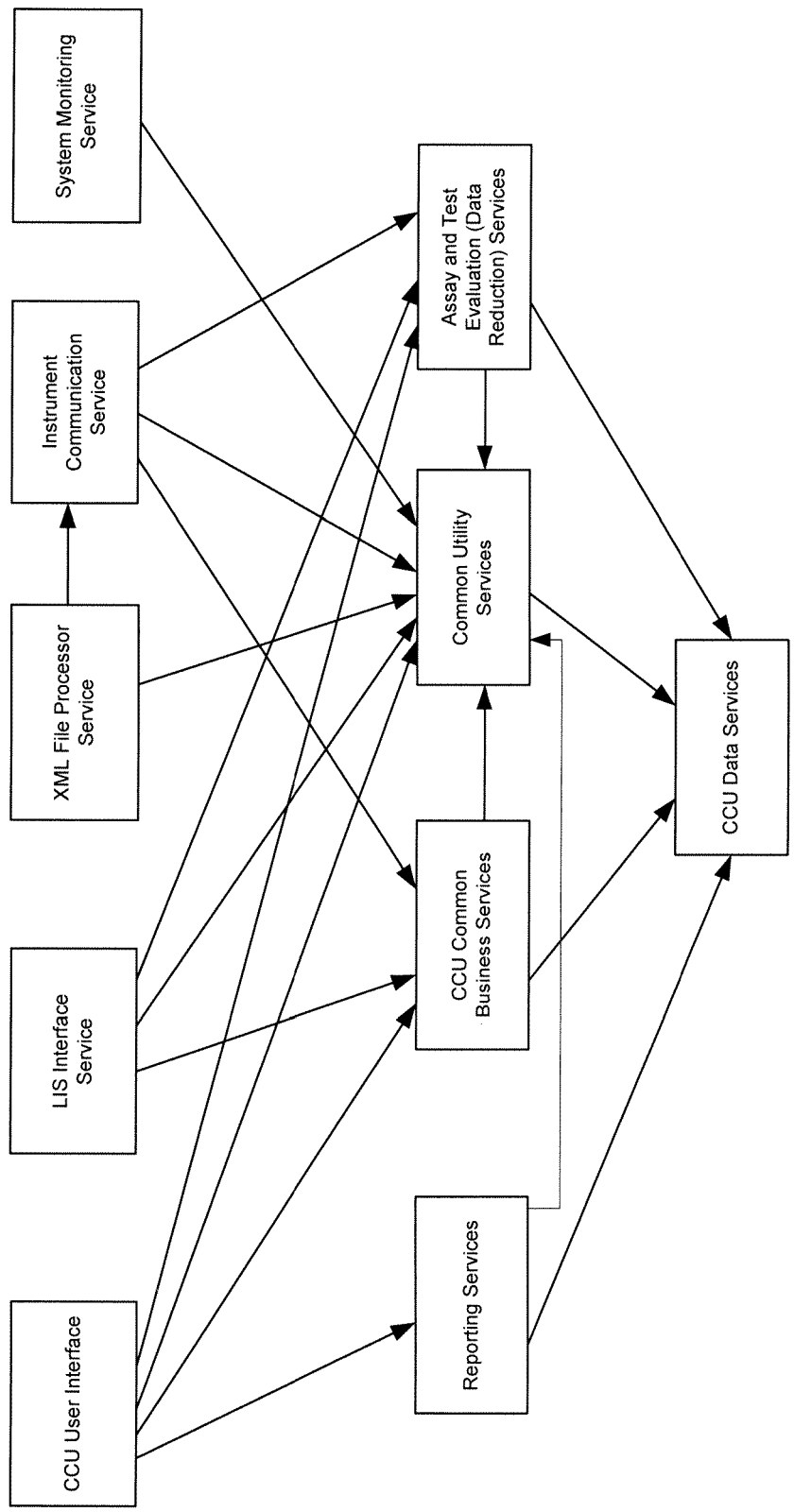
FIG. 9 is a diagram illustrating module dependencies and interactions, according to an embodiment.
Figure 10:
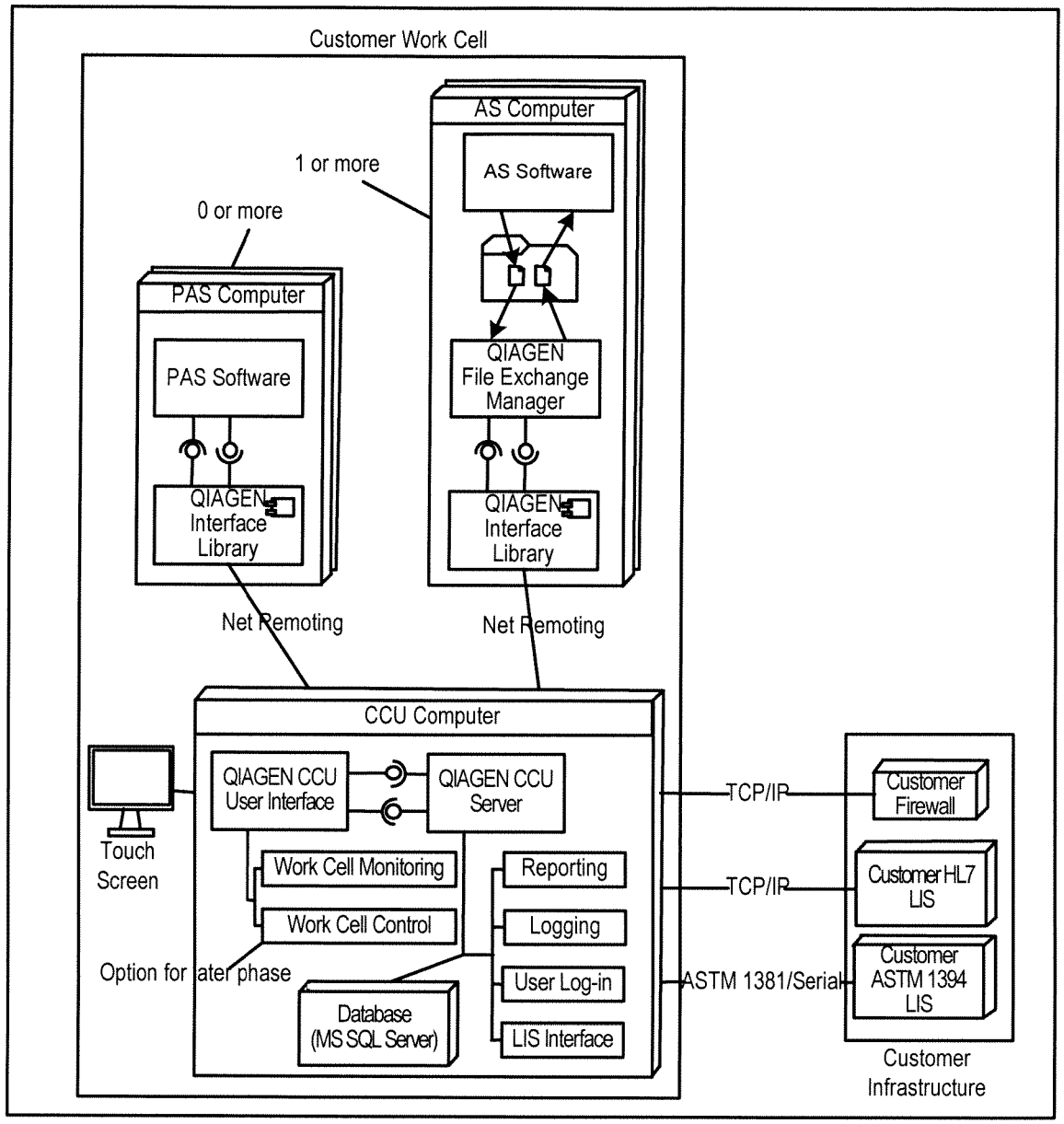
FIG. 10 depicts a diagram of a physical view of the CCU software in terms of the major software subcomponents of CCU, according to an embodiment.
Figure 11:
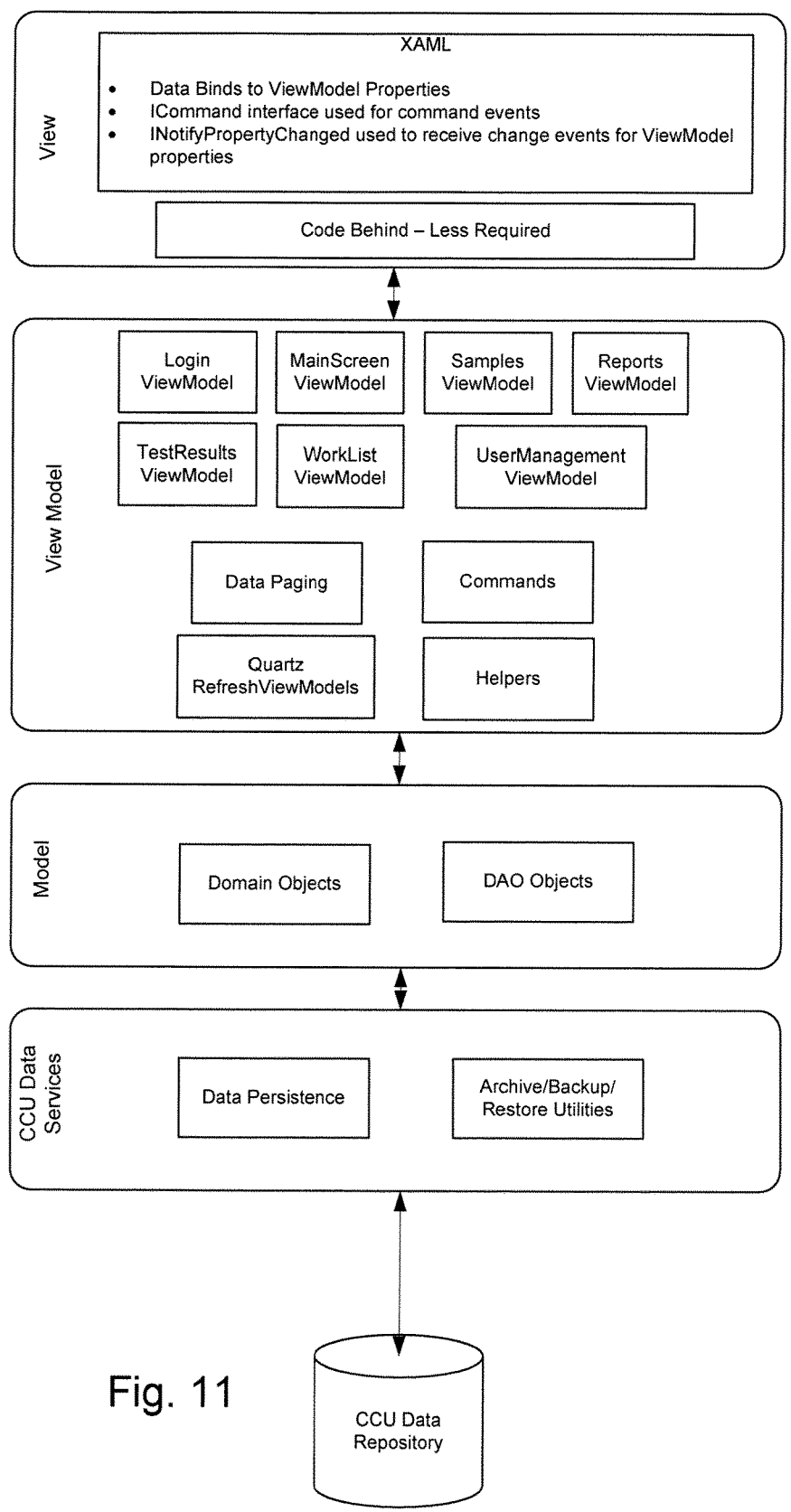
FIG. 11 shows a more detailed view of the MVVM design pattern implemented in the CCU Operator Interface, according to an embodiment.

FIG. 9 is a diagram illustrating module dependencies and interactions, according to an embodiment. FIG. 10 depicts a diagram of a physical view of the CCU software in terms of the major software subcomponents of CCU, according to some embodiments. FIG. 11 shows a more detailed view of the MVVM design pattern implemented in the CCU Operator Interface, according to some embodiments.

Figure 12:
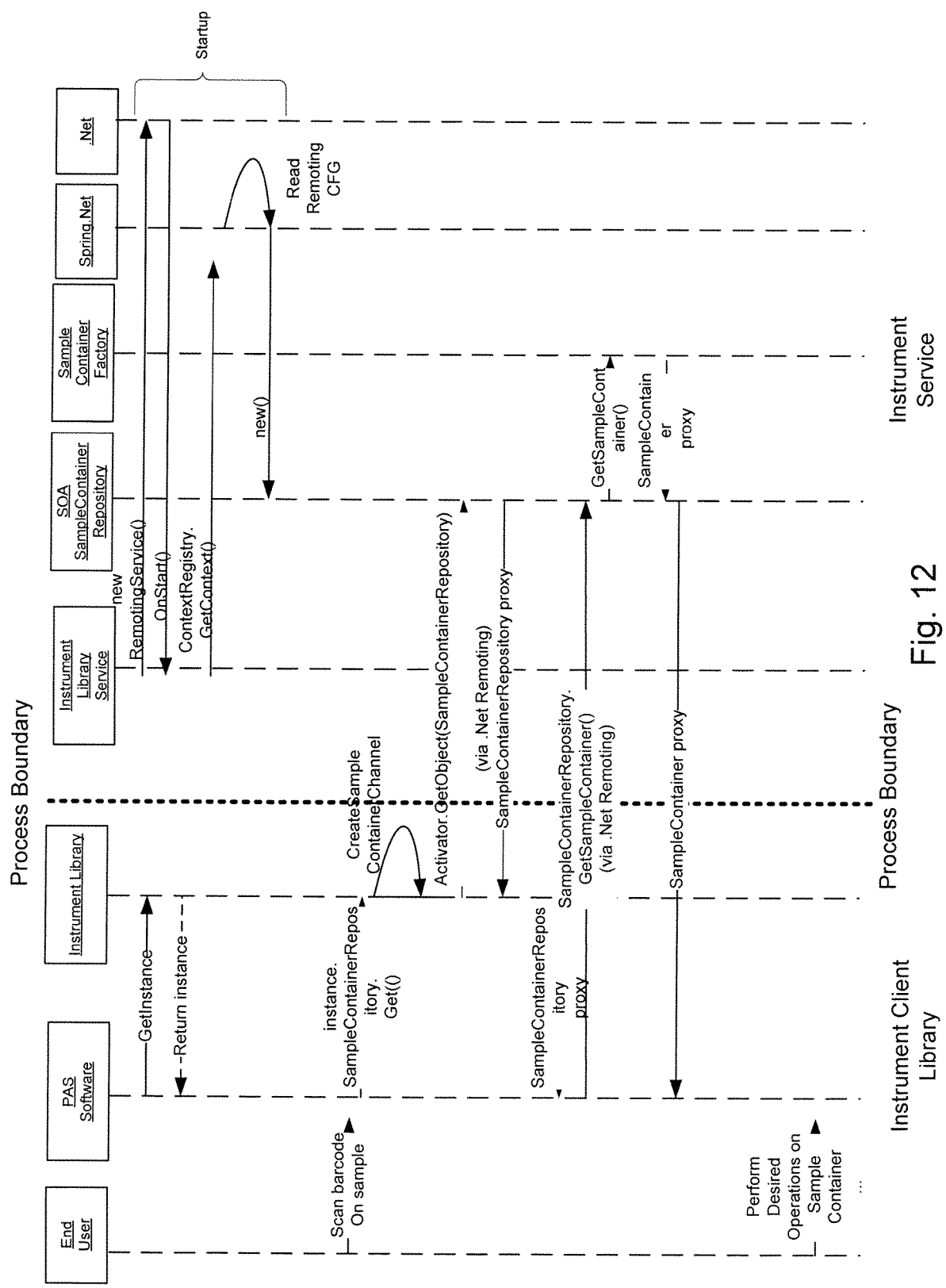
FIG. 12 is a sequence diagram illustrating communication between an Instrument Client Library and an Instrument Service, according to an embodiment.

FIG. 12 is a sequence diagram illustrating communication between an Instrument Client library and an Instrument Service, according to an embodiment The Instrument Client library may communicate to the Instrument Service through .Net Remoting. Net Remoting may be a service provided toy the .Net framework that may allow objects to communication across process boundaries and across the network. The interfaces to use .Net Remoting may be straightforward and, once a class is declared as "remoting enabled", the target and consumer source code look so different than if using local objects.

As illustrated in FIG. 12, the Instrument Giant Library may makes an explicit call to Activate a remote top-level service object. This "extra" code to obtain a reference to a service object may not be exposed to the end-consumer of the Instrument Client Library, such that the consumer of the library may not care or know that it is communicating with a remote service. Top-level service objects in the Instrument Service may be declared as "Server Activated Objects" (SAOs), meaning they may live on a server and a proxy object may be created on the client machine. They may be Singleton objects, as well, meaning they are created the first time when requested by a client, bet stay in existence indefinitely after created (until the service exits). Spring.Net through its integration with .Net Remoting, may instantiate one or mom top-level service objects, as shown in the sequence diagram in the "startup" phase. The Instrument Library Client interface may be very high-level and its interface may deal with large-grained operations like "get reagent container" and "save reagent container". According to some embodiments, them may be no direct database access from the client library or the application using the client library. One or mare database access operations may be performed by the Instrument library Service. When a high-level call is made to the Instrument Library the entire object graph may be made available to the caller, also, via .Net Remoting. The objects referenced by the high level object returned can be returned as a proxy or by value, depending epos how the class declaration is set up. Containers, wrappers, and repositories may be declared as proxy objects by inheriting from MarshalByRefObject, while non-container objects are declared using the Serializable attribute in the class definition and are returned by-value in the object graph. The library interaction may be designed abound the paradigm of "retrieve a lot of related data, work on it, save it all back when finished working on it".

Figure 13:
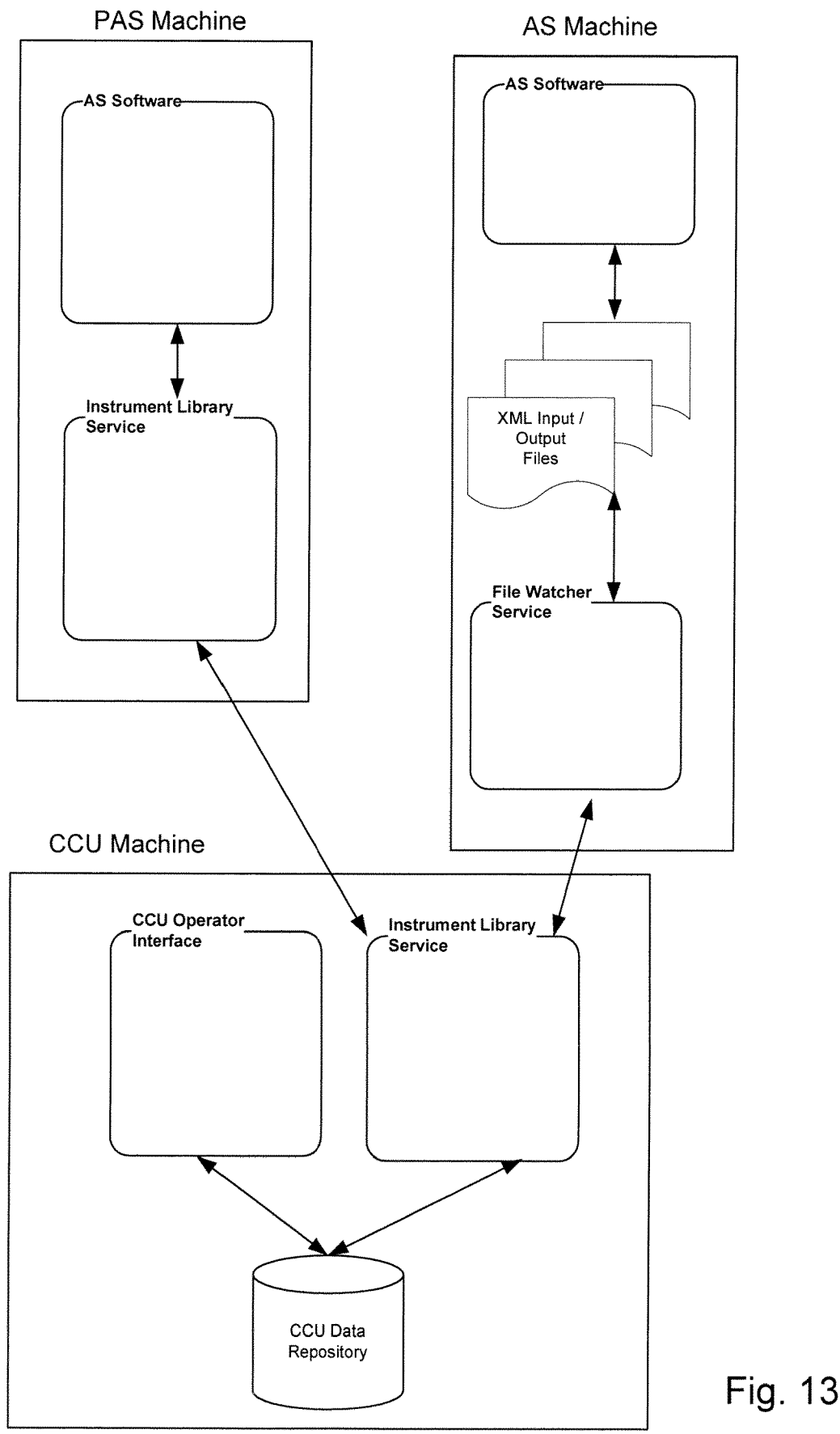
FIG. 13 is a diagram relating logical components of an AS, a CCU, and a PAS, to the physical component names, according to an embodiment.

FIG. 13 is a diagram relating logical components of an AS, a CCU, and a PAS, to the physical component names, according to an embodiment.

Figure 14:
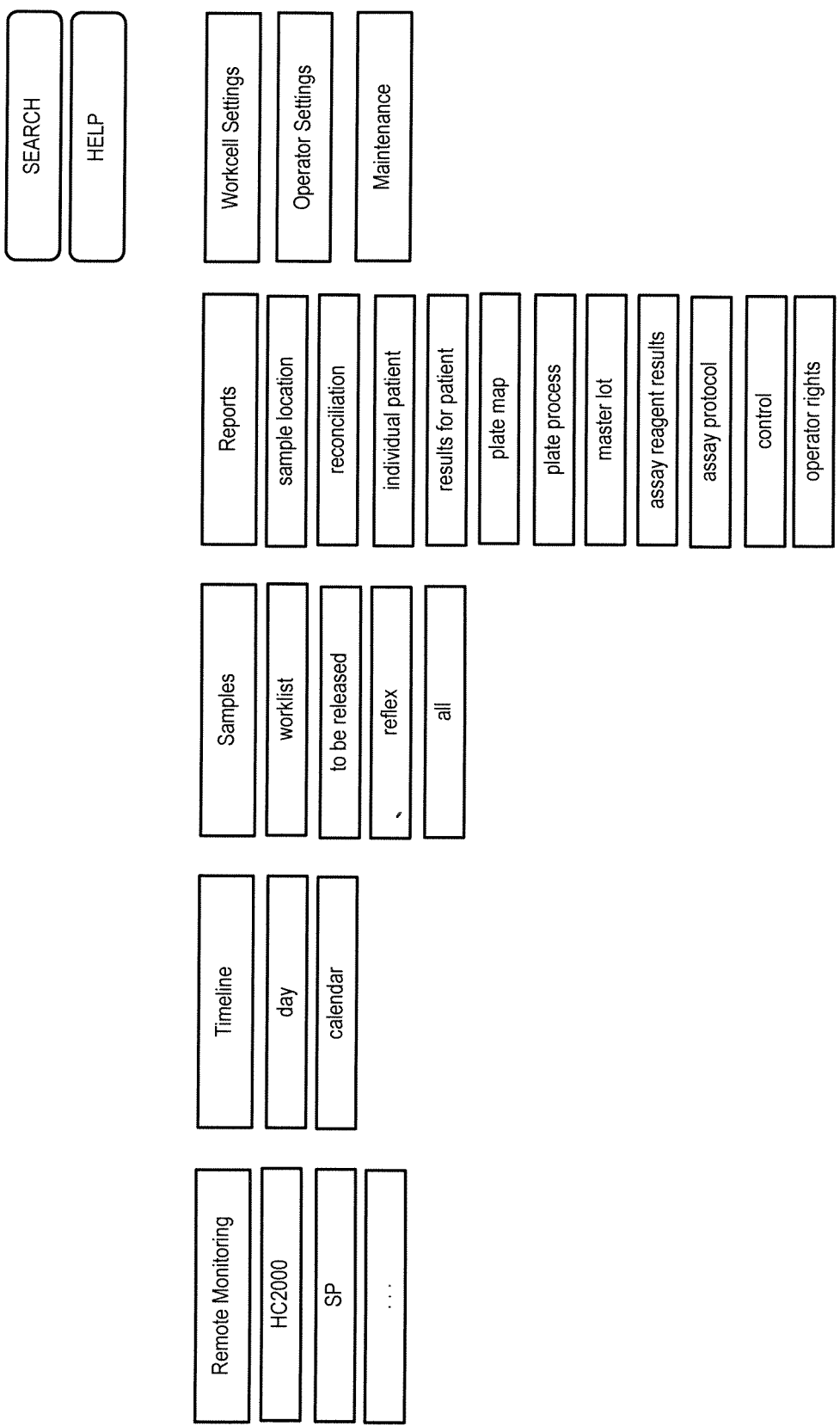
FIG. 14 depicts an exemplary organizational chart of interface screens, according to an embodiment.

FIG. 14 depicts an exemplary organizational chart of interface screens.

Figure 15:
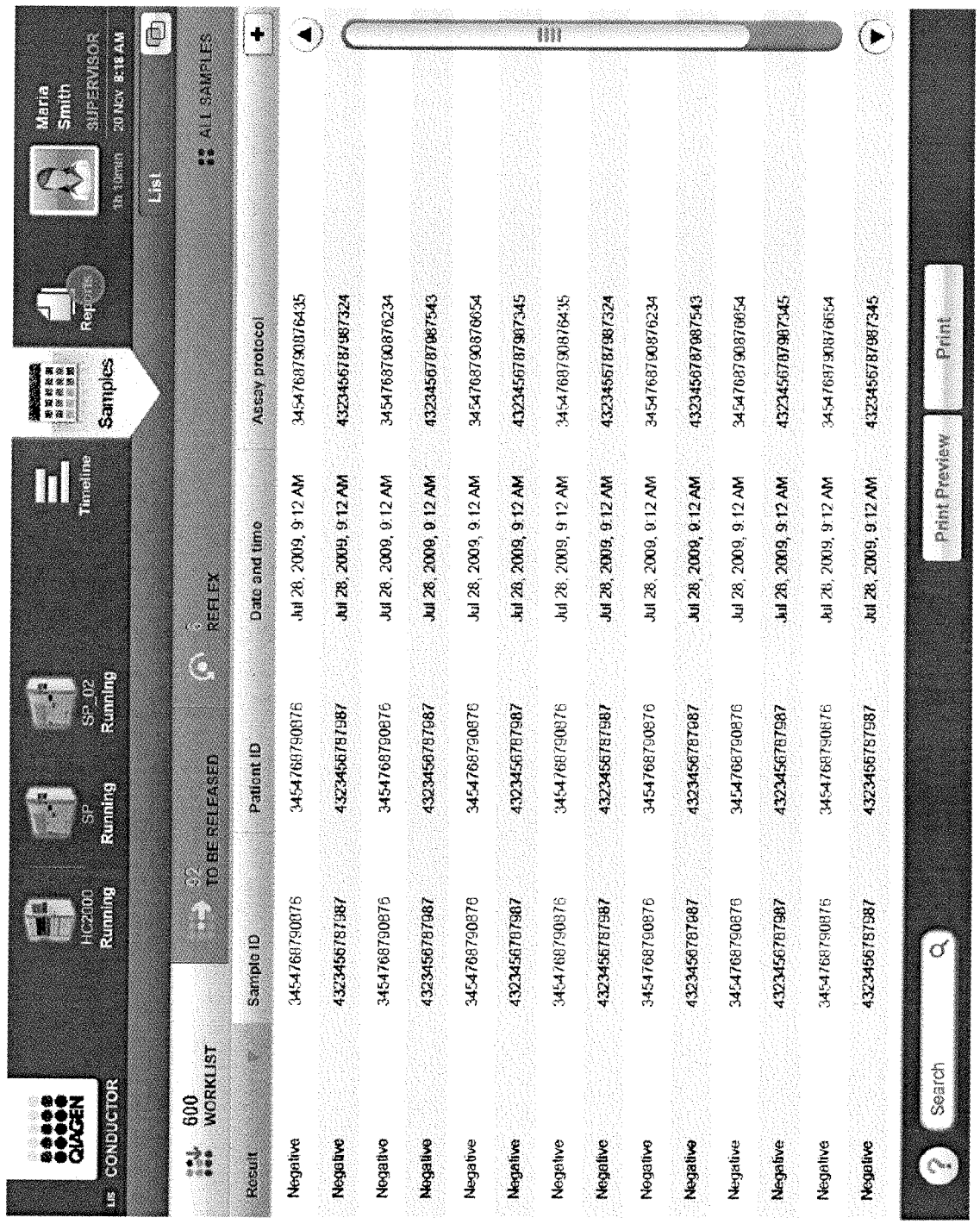
FIG. 15 depicts a user interface for viewing a sample worklist, according to an embodiment.

FIG. 15 depicts a user interface for viewing a sample worklist, according to an embodiment As illustrated in FIG. 15, a worklist may provide sample details including, but not limited to: a result, a sample ID, a patient ID, a sample date and time, and an assay protocol. A worklist may be sortable, filterable, and scrollable.

Figure 16:
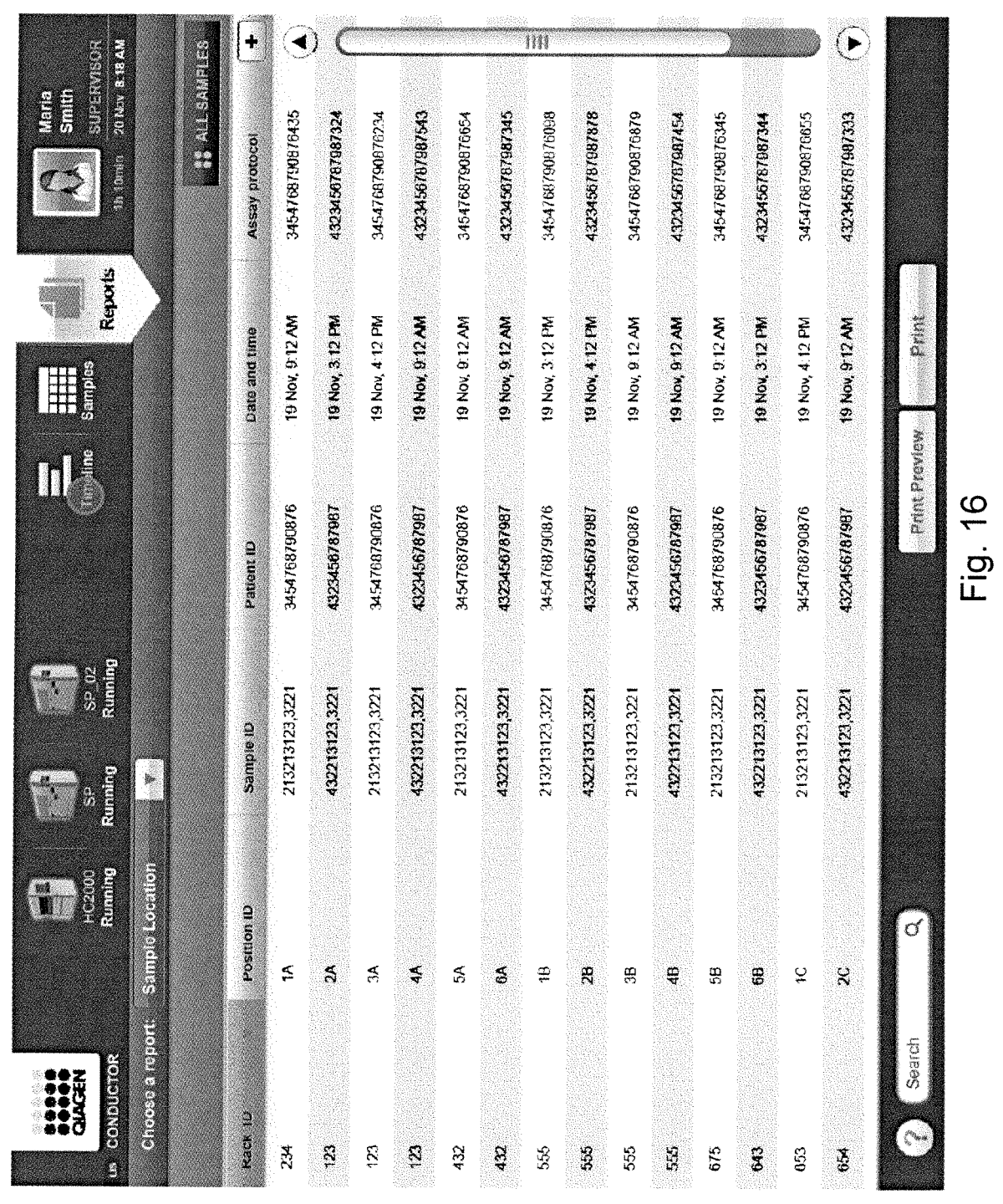

FIG. 16 depicts a user interface for viewing a sample location report, according to an embodiment A sample location report may include location details for a sample such as, for example, a rack id, a position id, a sample id, a patient id, and sample dale and time, and an assay protocol A sample location report may be sortable, filterable, and scrollable.

Figure 17:
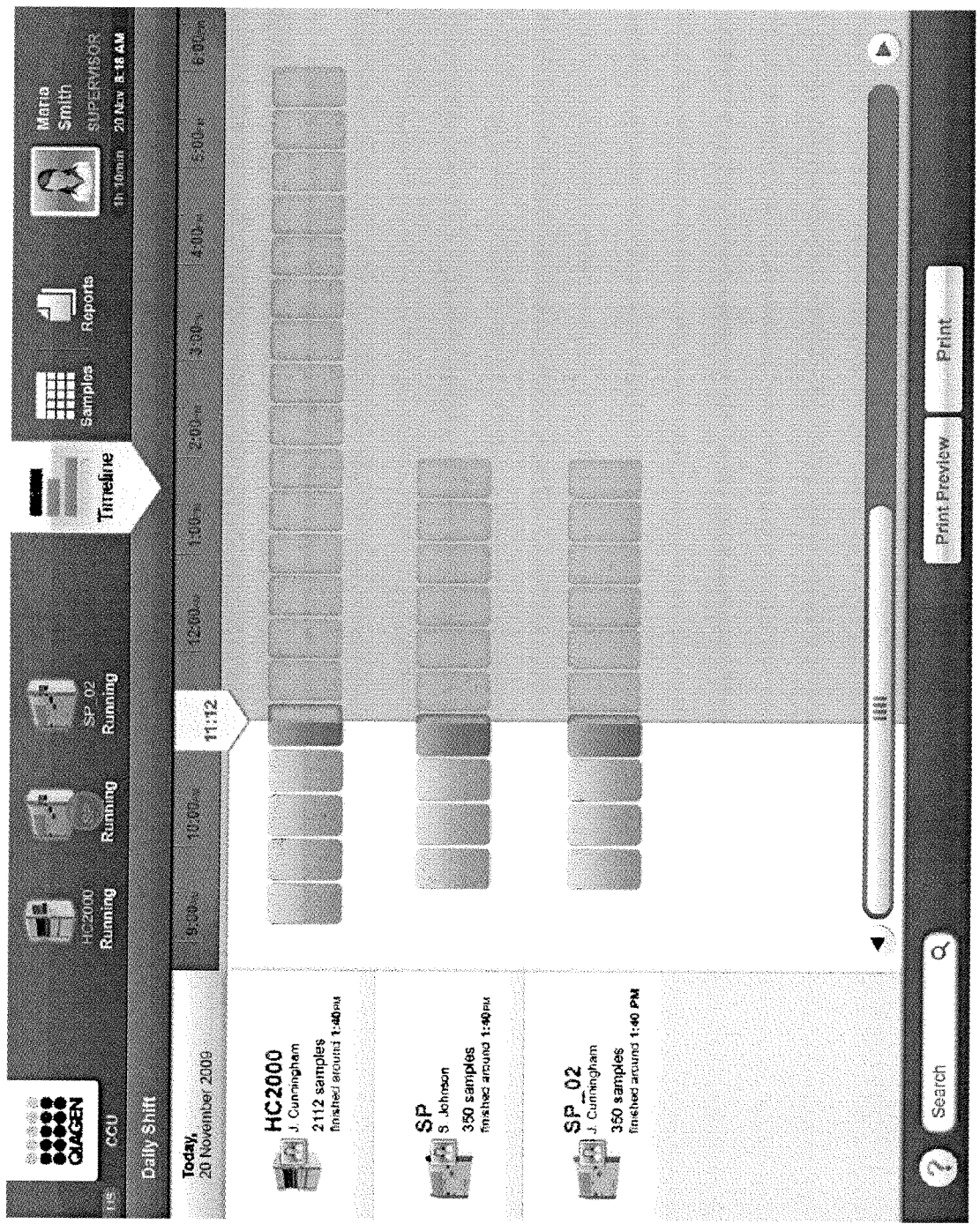
FIG. 17 depicts a user interface for viewing preparation and testing timelines for Analytical and Pre-Analytical systems, according to an embodiment.

FIG. 17 depicts a user interface for viewing preparation and testing timelines for Analytical and Pre-Analytical systems, according to an embodiment. Timelines may include a start time for one or more jobs (e.g., pre-analytical processing and analytical processing), a current time, a projected end time, an instrument operator, a number of samples being processed, and other timeline details.

Figure 18:
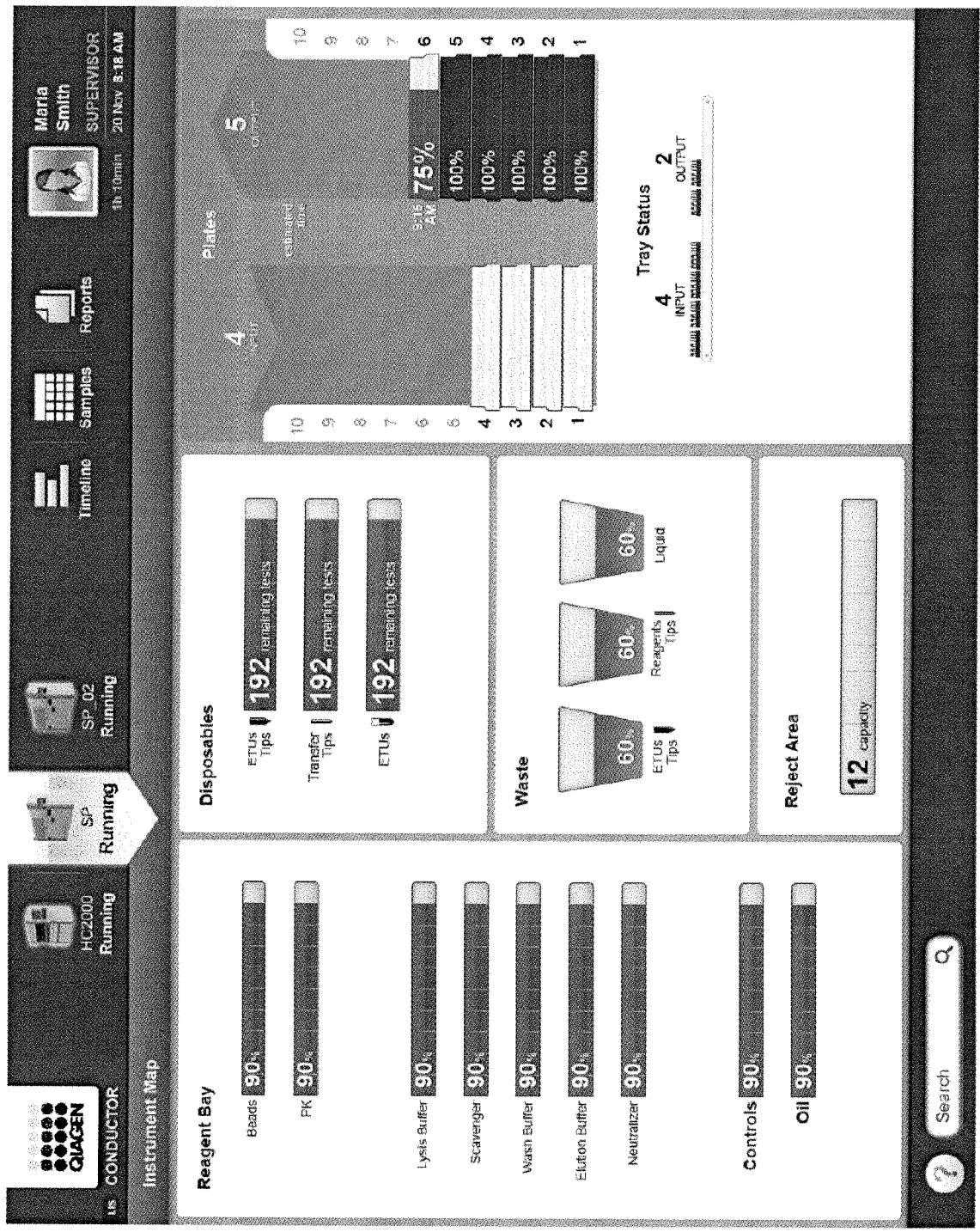
FIG. 18 depicts a user interface for remote monitoring of a pre-analytical system, according to an embodiment.

FIG. 18 depicts a user interface for remote monitoring of a pre-analytical system, according to an embodiment Pre-analytical system monitoring details may include, for example, a current status of materials in one or more reagent bays (e.g., beads, buffer, controls, oil, etc.), a current status of disposable items (e.g., ETU tips, transfer tips, ETUs, etc.), a current status of one or more waste containers, a current status of a reject holding area, a current input status (e.g., plates queued for input), and a current status of an output area (e.g., plates ready for output to an AS).

Figure 19:
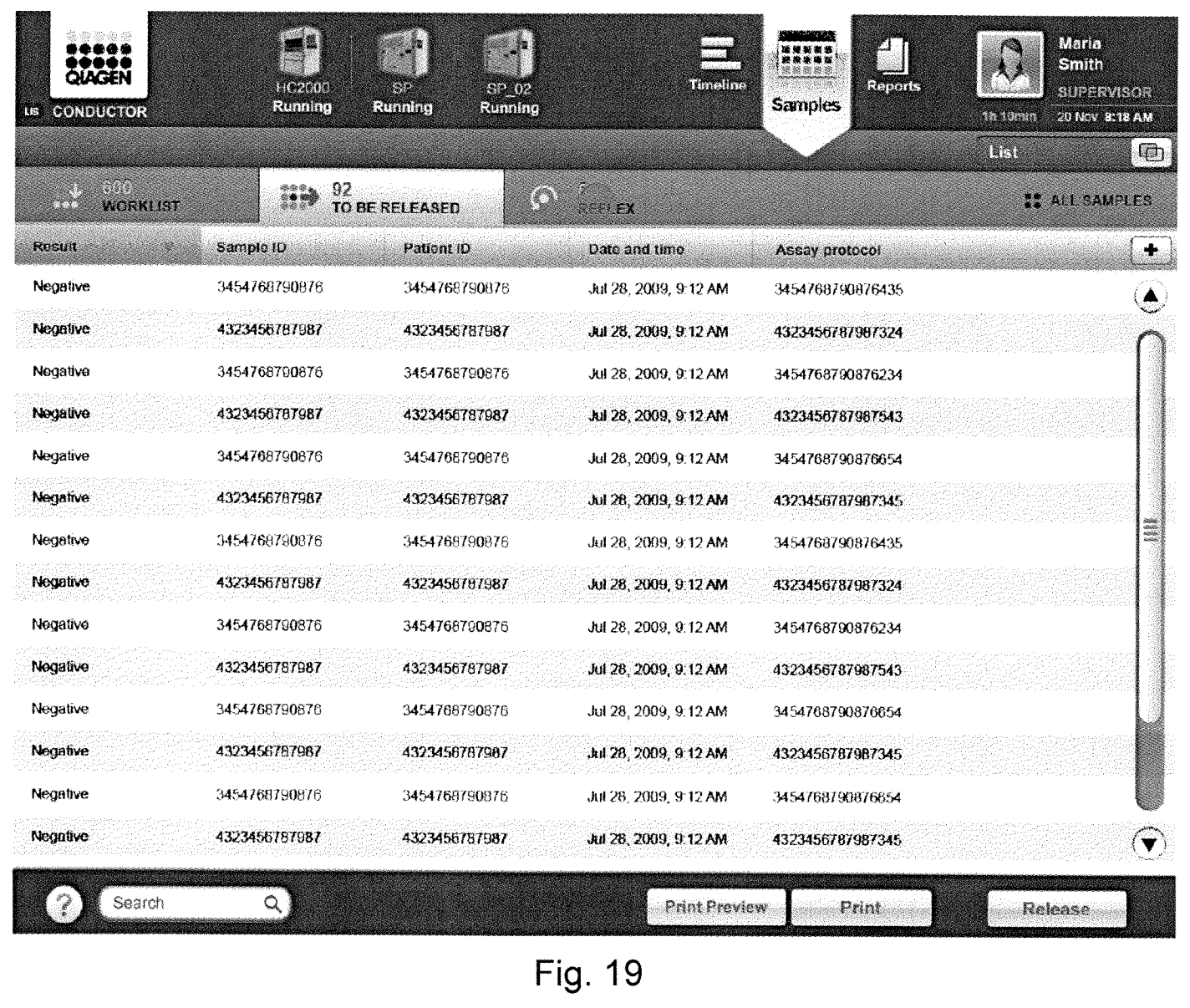

FIG. 19 depicts a user interface for releasing samples from a worklist for genotyping, according to an embodiment. An interface for releasing samples from a worklist may provide a count of samples to be released and individual sample details.

Figure 20:
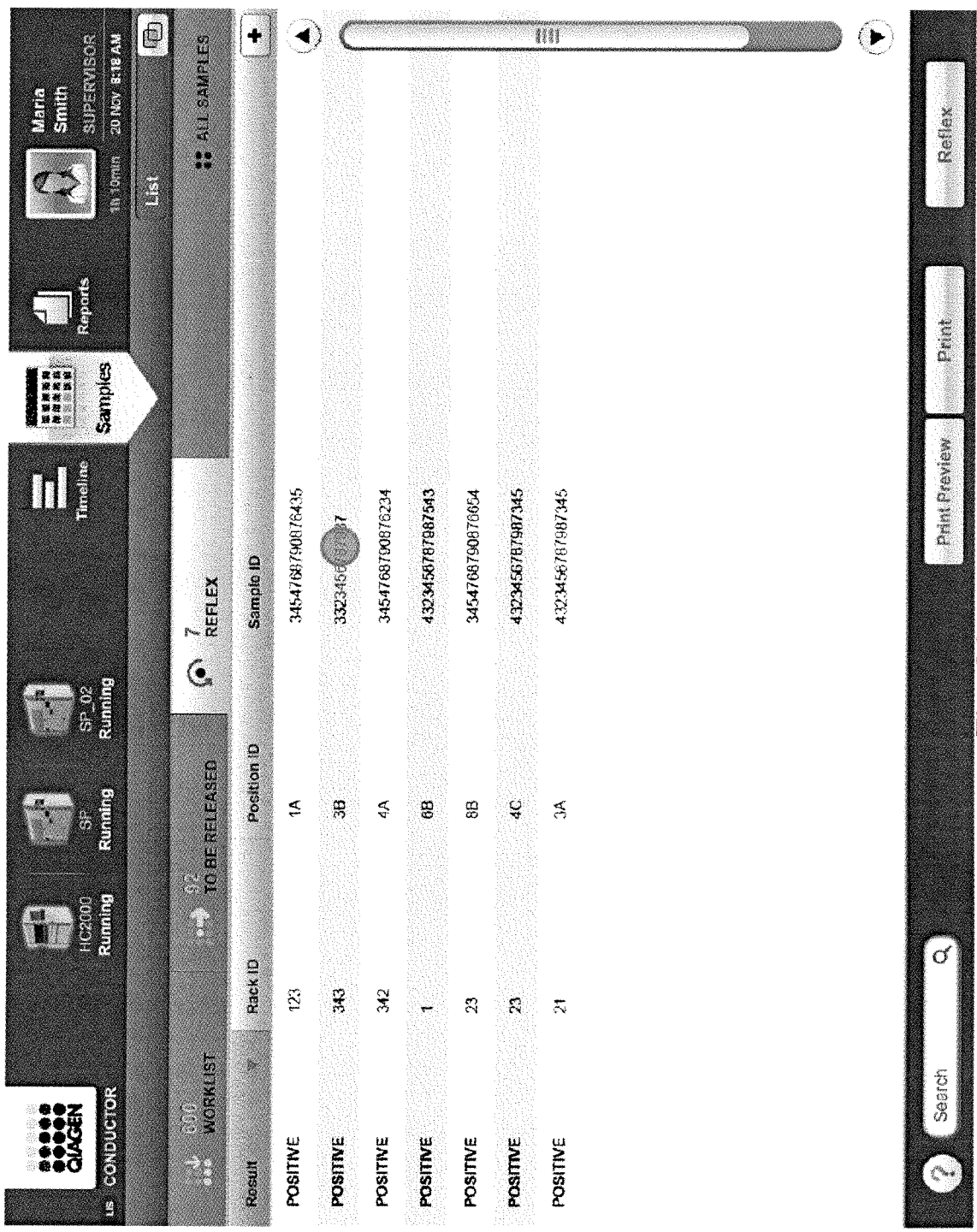
FIG. 20 depicts a user interface for reflex sample information verification, according to an embodiment.

FIG. 20 depicts a user interface for reflex sample information verification, according to an embodiment. Sample information may include a result, a rack id, a position id, and a sample id. A user control may be provided to trigger reflex testing of one or more samples.

Figure 21:
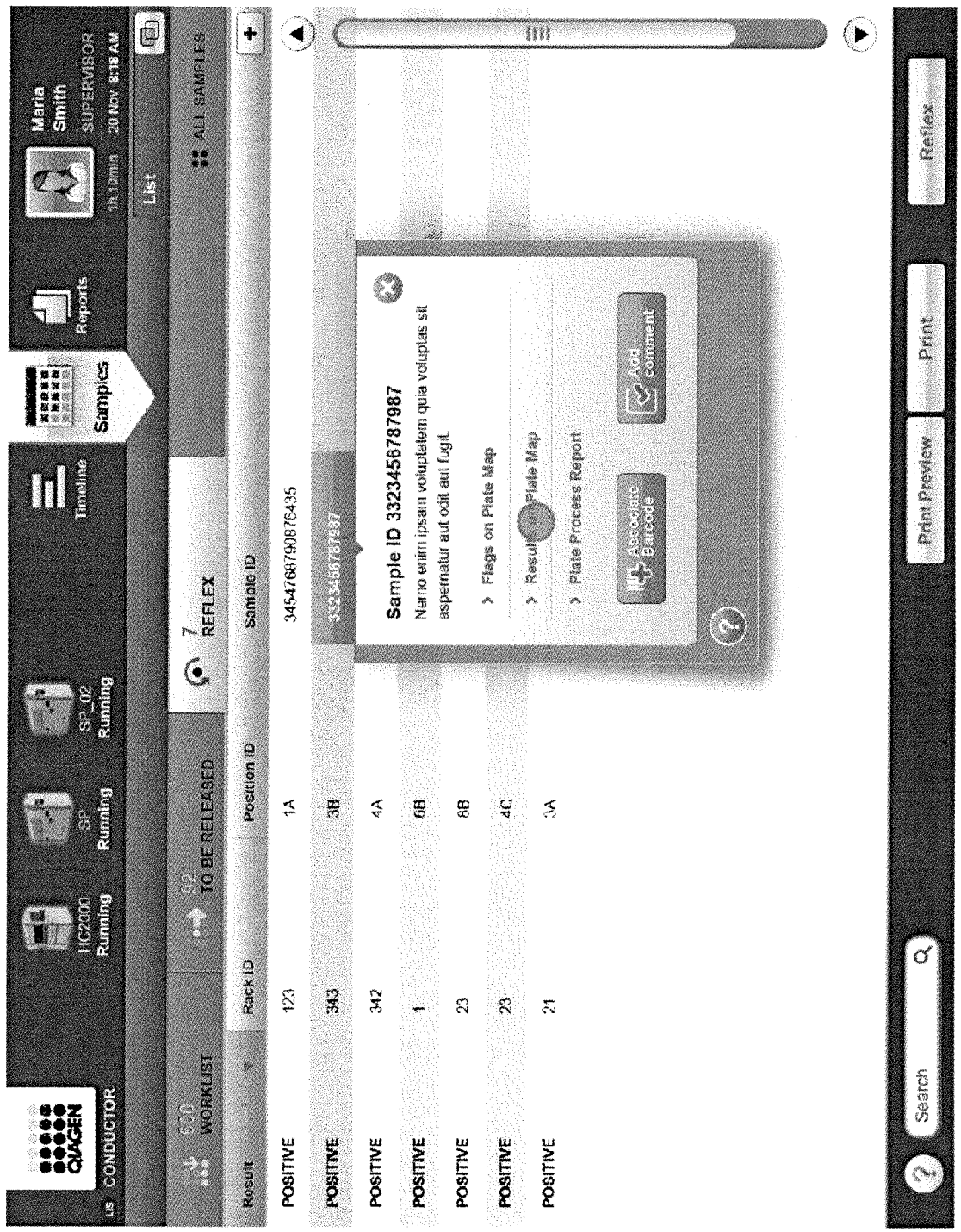
FIG. 21 depicts a user interface for selecting a view of reflex information according to an embodiment.

FIG. 21 depicts a user interface for selecting a view of reflex information according to an embodiment.

Figure 22:
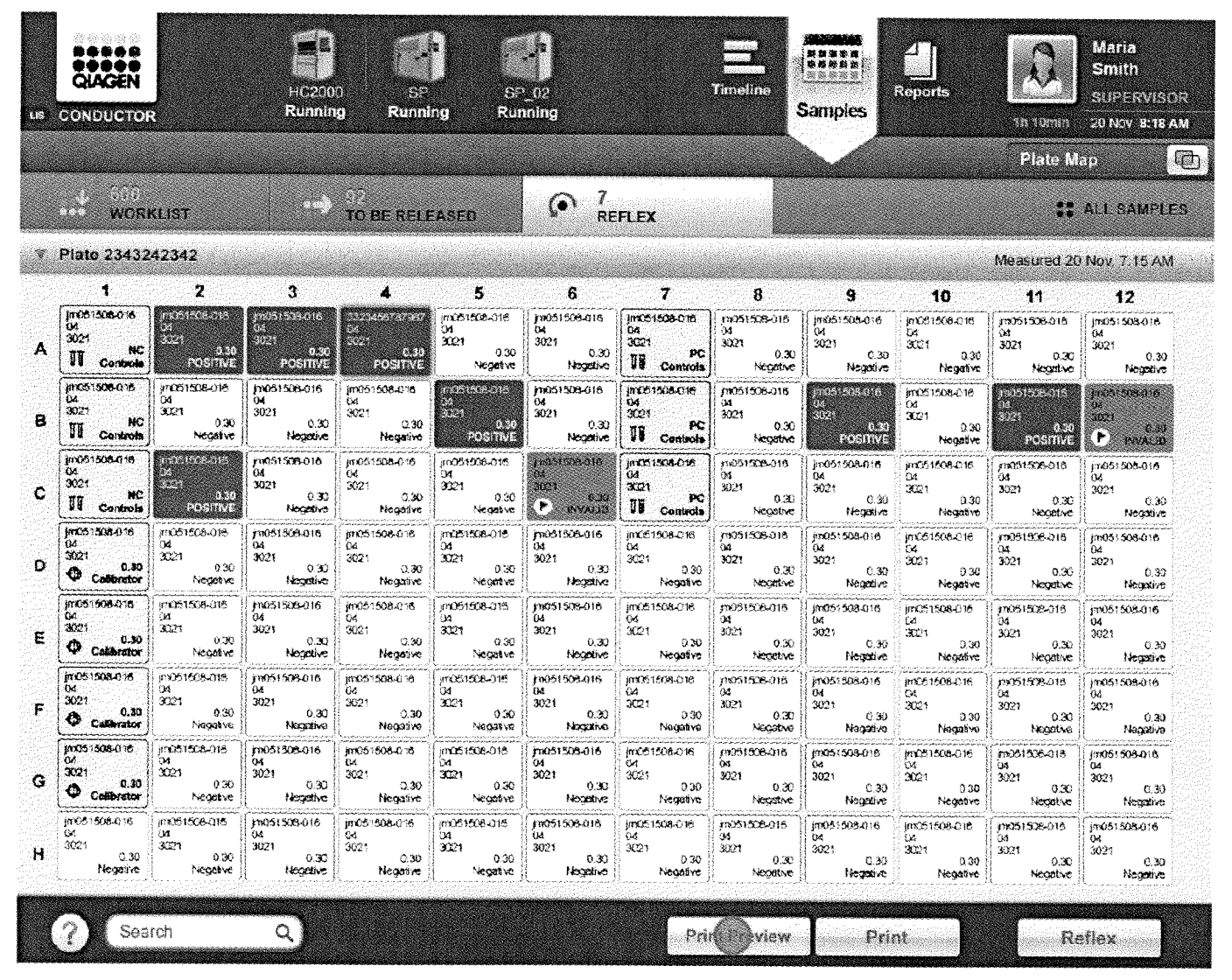

FIG. 22 depicts a user interface for a plate map highlighting samples selected for reflex testing, according to an embodiment.

Figure 23:
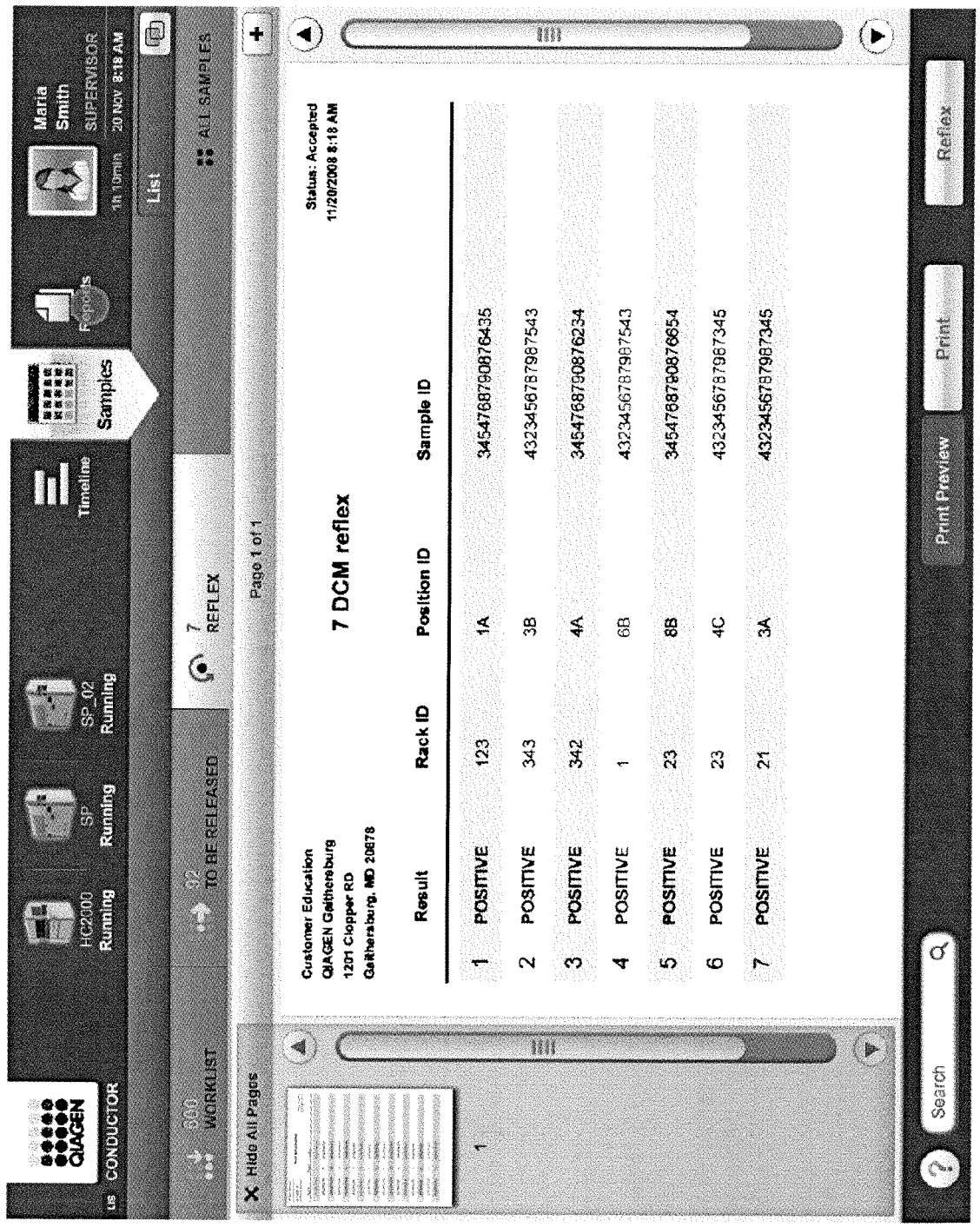
FIG. 23 depicts a user interface for sample reflex listing, according to an embodiment.

FIG. 23 depicts a user interface for sample reflex listing, according to an embodiment.

FIG. 24 depicts a user interface for sample location reporting for reflex samples, according to an embodiment.

Figure 25:
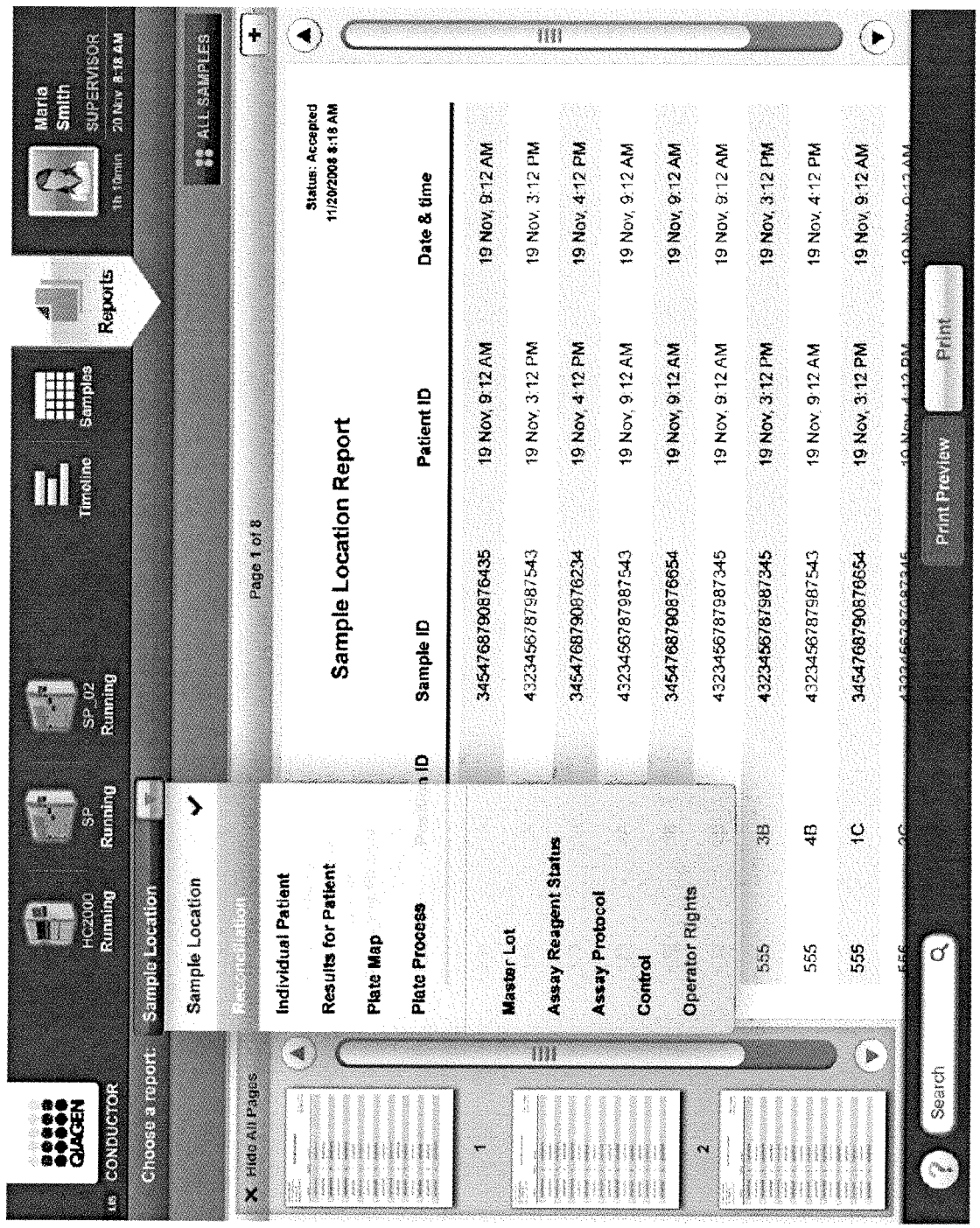
FIG. 25 depicts a user interface for selecting reports, according to an embodiment.

FIG. 25 depicts a user interface for selecting reports, according to an embodiment.

Figure 26:
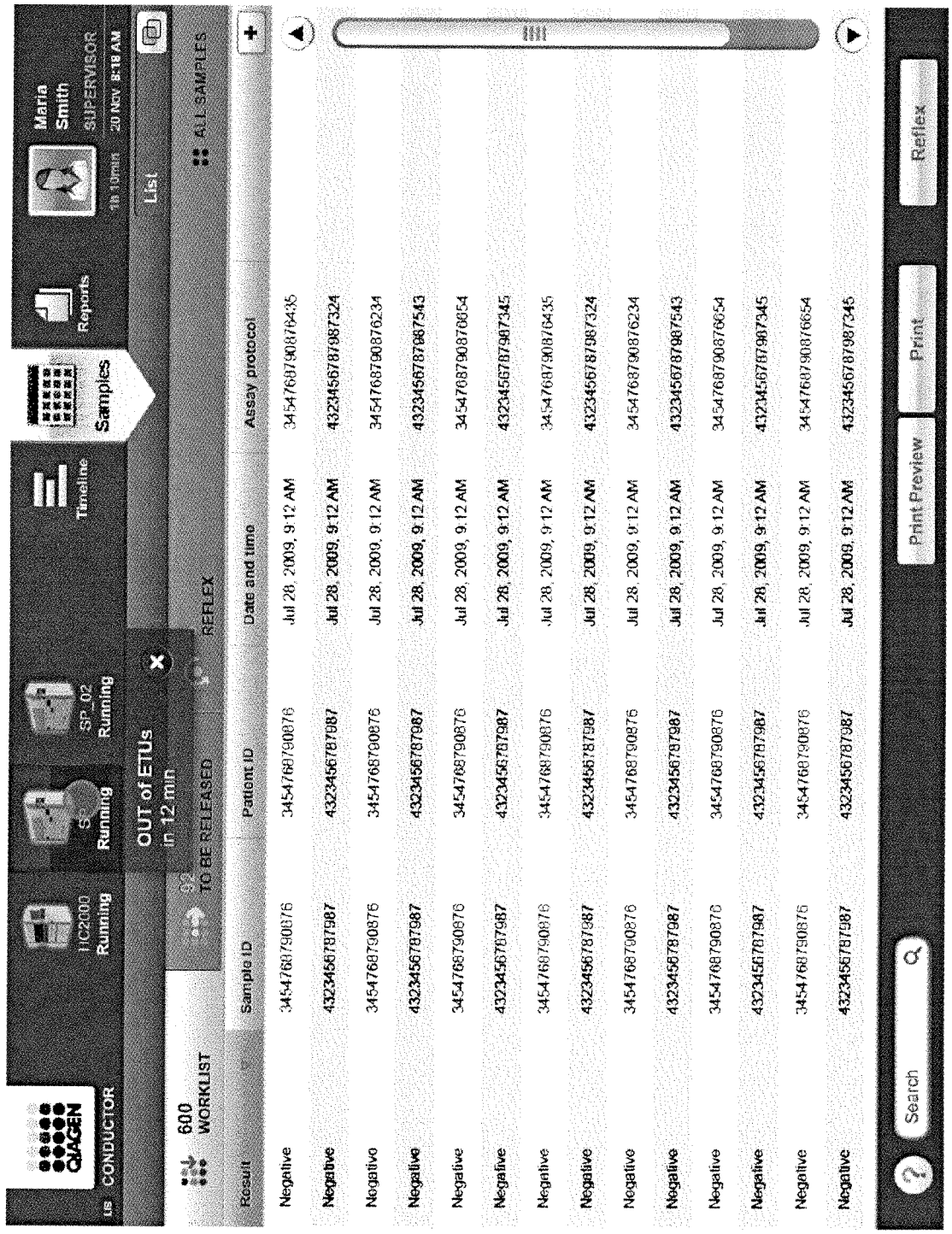
FIG. 26 depicts a user interface for alerts associated with attached instruments, according to an embodiment.

FIG. 26 depicts a user interface for alerts associated with attached instruments, according to an embodiment. As depicted, a user interface may contain a dashboard or other area displaying icons or other indicators of instalments associated with a CCU. An alert may be associated with an icon of an instrument and may be selectable for a user to obtain more information.

Figure 27:
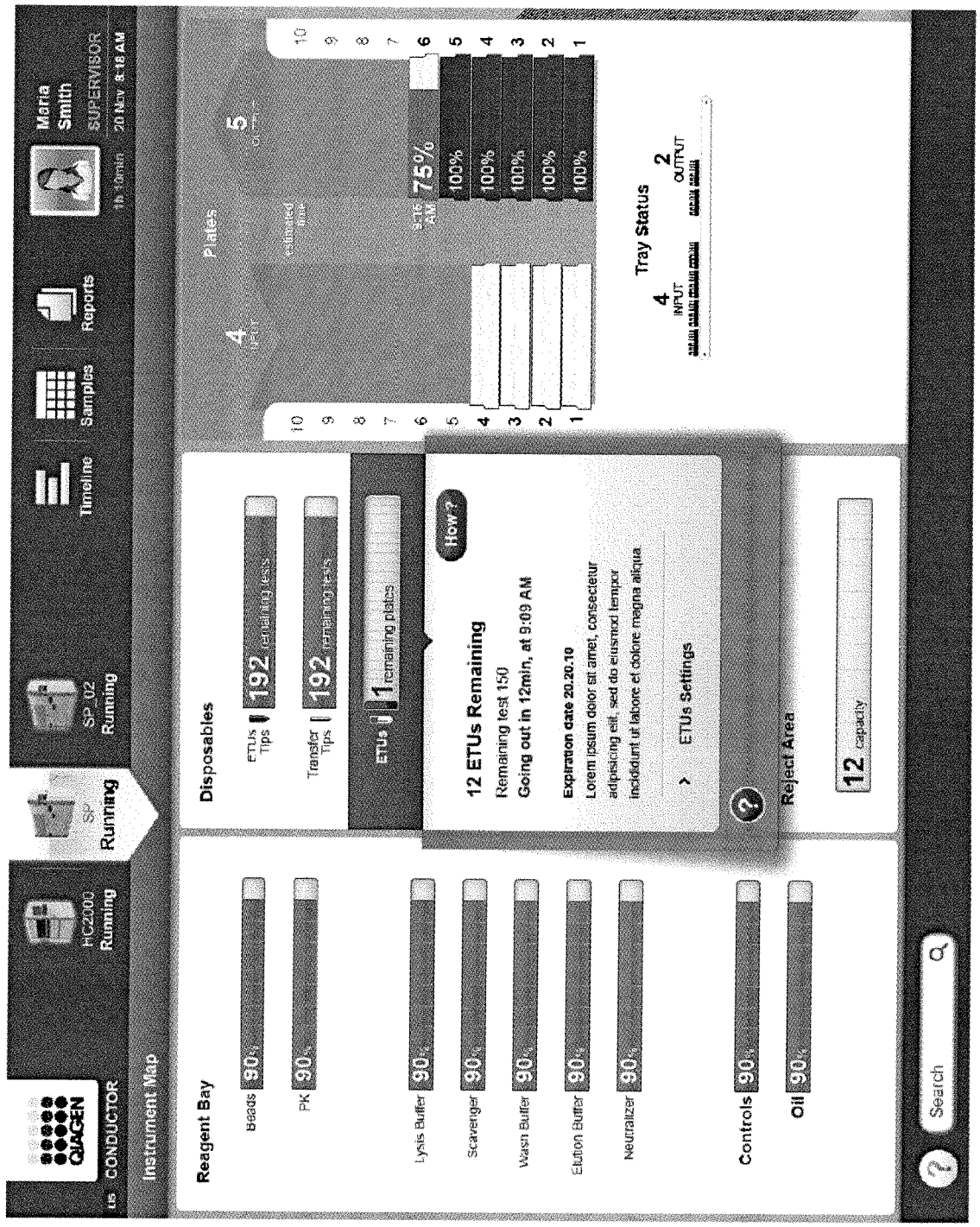
FIG. 27 depicts a user interface displaying an alert detail, according to an embodiment.

FIG. 27 depicts a user interface displaying an alert detail, according to an embodiment. As depicted m alert detail may provide instrument status details (e.g., an AS or a PAS running low on a reagent, a disposable item, or other supplies). Alerts may also signal completion of a process, an error, or other conditions.

Figure 28:
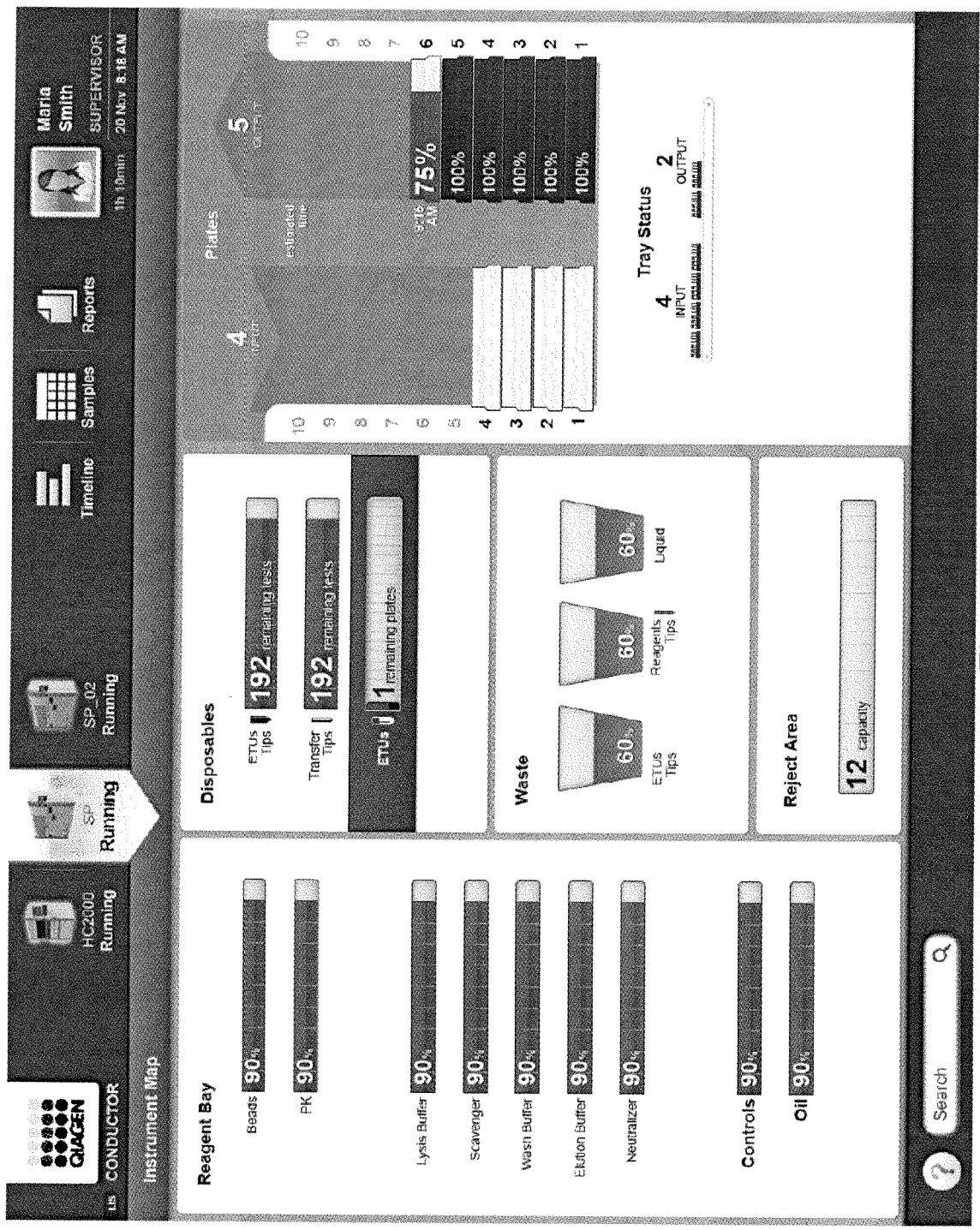
FIG. 28 depicts a user interface for viewing instrument status information, according to an embodiment.

FIG. 28 depicts a user interface for viewing instrument status information, according to an embodiment. An instrument status information interface may allow a CCU operator to remotely diagnose a condition triggering an alert.

Figure 29:
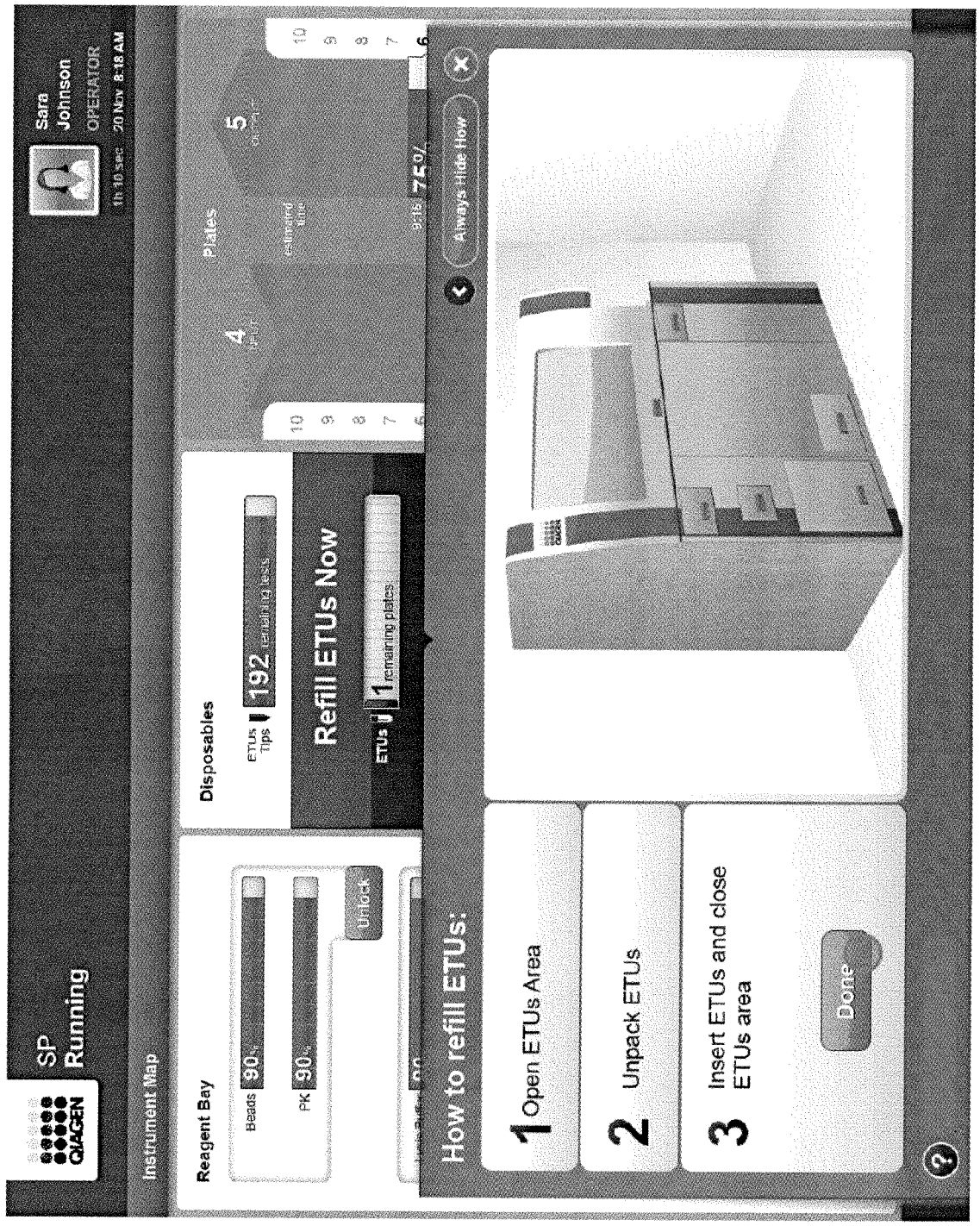
FIG. 29 depicts a user interface for providing operator help, according to an embodiment.

FIG. 29 depicts a user interface for providing operator help, according to an embodiment. Operator help may be associated with an alert and may provide instructions allowing an operator to resolve a condition triggering an alert.

Figure 30:
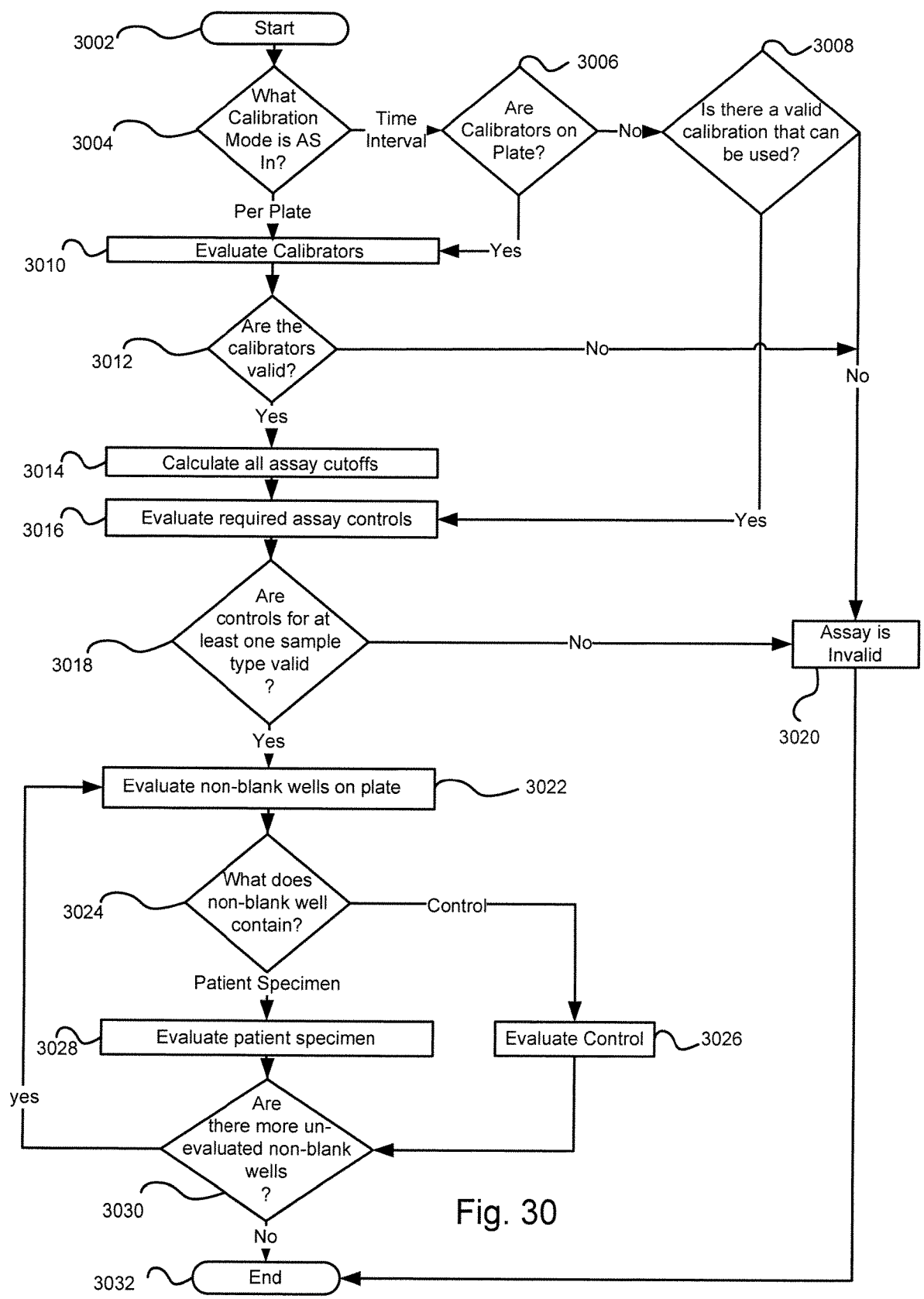
FIG. 30 depicts a method for analyzing a plate processed on an Analytical System, according to an embodiment.

FIG. 30 depicts a method for analyzing a plate that was processed on an Analytical System, according to an embodiment. The method may begin at block 3002. When plate measurement is initiated, software may be provided with a plate background value from a luminometer at the beginning plate measurement. The following background correction algorithm may be applied to one or more measured wells on a plate prior to initiating any of the data reduction. This may apply to calibrators, controls, and patient specimens on a plate. The initial RLU value measured for a well may be referenced as Well RLURaw. For each measured well on the plate, the reported RLU value for the well may be calculated as follows:

Well RLUcorrected=Well RLURaw–Plate Background

If the Well RLUCorrected value is determined to be less than zero, then the Well RLUcorrected value may be set to zero.

At block 3004, calibration mode of an AS may be determined. If the calibration mode is time interval, the method may continue at block 3006. If the calibration mode is per plate, the method may continue at block 3010.

At block 3006, it may be determined whether calibrators are on a plate. If calibrators are on a plate, the method may continue at block 3010. If calibrators are not on a plate, the method may continue at block 3008.

At block 3008, it may be determined whether there is a valid calibration that can be used. If there is a valid calibration that can be used, the method may continue at block 3016. If there is not a valid calibration that can be used the assay may be indicated as invalid at block 3020.

At block 3010 calibrators may be evaluated. Evaluation of a calibrator is discussed in further detail in reference to FIG. 31 below.

At block 3012 it may be determined whether the calibrators are valid. If the calibrators are valid the method may continue at block 3014. If the calibrators are not valid the method may continue at block 3020.

At block 3014, assay cutoff values may be calculated. Assay controls may be evaluated at block 3016.

At block 3018 it may be determined whether controls for at least one sample type are valid. If controls for at least one sample type are valid, the method may continue at block 3022. If controls are not valid for at least one sample type the method may continue at block 3020.

At block 3020, an assay may be determined to be invalid and the method may end at block 3032.

At block 3022, non-blank wells on a plate may be evaluated. At block 3024, the content of a non-blank well may be determined. If a non-blank well contains a control, the method may continue at block 3026. If a non-blank well contains a patient specimen, the method may continue at block 3028.

At block 3026 a control may be evaluated. Evaluation of a control is discussed in further detail in reference to FIG. 32 below.

At block 3028, a patient specimen may be evaluated.

At block 3030, it may be determined whether any more un-blank wells remain for evaluation on a plate. If further un-blank wells are to be evaluated, the method may return to block 3022. If no further un-blank wells are to be evaluated, the method may end at block 3032.

Figure 31:
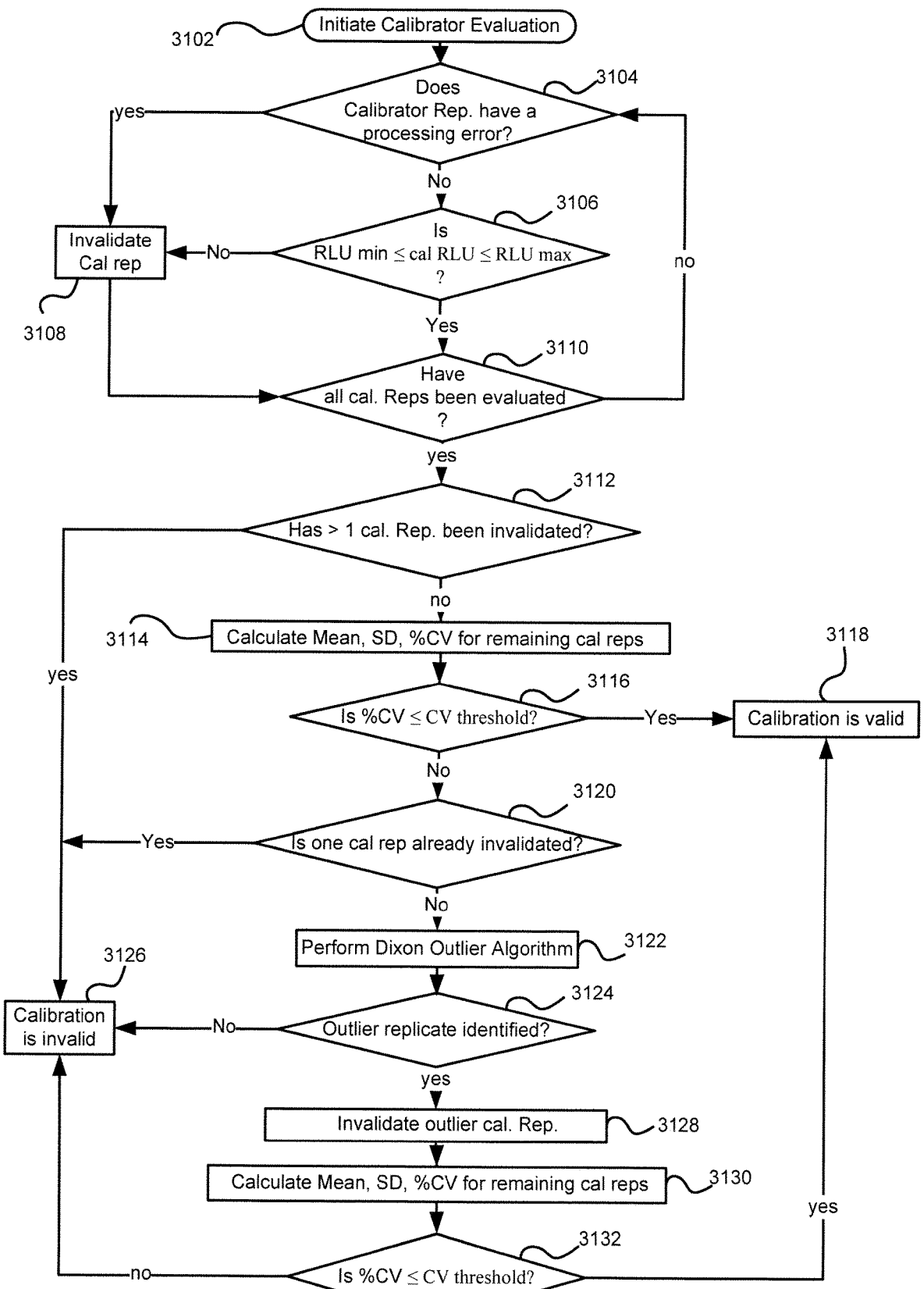
FIG. 31 depicts a method for analyzing a calibrator replicate, according to an embodiment.

FIG. 31 depicts a method for analyzing a calibrator replicate according to an embodiment. According to some embodiments, calibrators may be evaluated on a per-shift or a per-plate basis, depending on mode specified for the assay.

In per shift calibration mode, each plate references one set of valid calibrators for the entire shift. At block 3102, calibrator evaluation may be initiated.

At block 3104, it may be determined if more than one calibrator replicate has a processing error. If more than one calibrator replicate has a processing error, the calibrator replicate may be marked as invalid at block 3108. If one or no calibrator replicates have processing errors, the method may continue at block 3016.

At block 3106 the Relative Light Unit (RLU) of a calibrator replicate may be compared against specified minimum mid maximum values. If the RLU value of the calibrator replicate falls within specified values, the method may continue at block 3110. If the RLU value of the calibrator replicate falls outside of specified values, the calibrator replicate may be marked as invalid at block 3108.

At block 3110 it may be determined whether all calibrator replicates have been evaluated. If all calibrator replicates have been evaluated, the method may continue at block 3112. If more calibrator replicates remain for evaluation the method may return to block 3104.

At block 3112 it may be determined whether more than one calibrator replicate has been indicated as invalid. If more than one calibrator replicate has been indicated as invalid, the calibration may be determined to be invalid at block 3126. If one or no calibrator replicates have been indicated as invalid the method may continue at block 3114.

At block 3114, the mean, the standard deviation, and the percentage of a coefficient of variation may be calculated for a calibrator replicate. At block 3116, the percentage of the coefficient of variation for a calibrator replicate may be compared against a specified maximum value. If the percentage of the coefficient of variation for a calibrator replicate is less than or equal to a specified maximum threshold, the calibration may be indicated as valid at block 3118. If the percentage of the coefficient of variation for a calibrator replicate exceeds a specified threshold, the method may continue at block 3120.

At block 3120 it may be determined whether one calibrator replicate has already been invalidated. If a calibrator replicate has already been invalidated the calibration may be determined to be invalid at block 3126. If no calibrator replicate has already been invalidated, the method may continue to block 3122.

At block 3122, a dixon outlier algorithm may be performed. According to some embodiments, the Dixon Outlier Algorithm may only be applied if there are at least three calibrator replicates to analyze. The software may sort the non-validated replicates from lowest to highest RLU. The software may calculate $R_{high}$ and $R_{low}$ as follows:

$$R_{high}=(X_n-X_{(n-1)})/(X_n-X_1)$$

$$R_{low}=(X_2-X_1)/(X_n-X_1)$$

where $X_1$, $X_2$, etc . . . is a replicate RLU (sorted from low=1 to high=n), and n is the number of replicates. The scenario where $X_n-X_1$ would always lead to a division by zero error. However, because the calibrator replicates are sorted low to high, if $X_n=X1$ the calibrators may pass the % CV check and the Dixon Outlier Algorithm may not be applied.

The software may determine $X_n$ as an outlier, if $R_{high}$>r10(n), where r10(n), is determined from the table below for an alpha of 0.01.

The software may determine $X_1$ as an outlier, if $R_{low}$>r10(n), where r10(n), is determined from the table below for an alpha of 0.01.

According to some embodiments, only one calibrator replicate may be rejected.

| Number of Calibrator Replicates (n) | r10(n) | Alpha = 0.01 |
|---|---|---|
| 3 | r10(3) | 0.988 |
| 4 | r10(4) | 0.889 |
| 5 | r10(5) | 0.780 |
| 6 | r10(6) | 0.698 |

At block 3124 if an outlier replicate has not been identified, the calibration may be determined to be invalid at block 3126. If an outlier replicate has been identified the identified outlier calibrator replicate may be indicated as invalid at block 3128.

At block 3130, the mean, the standard deviation, and the percentage of a coefficient of variation may be calculated for the remaining calibrator replicates. At block 3132, the percentage of the coefficient of variation for a calibrator replicate may be compared against specified maximum value. If the percentage of the coefficient of variation for a calibrator replicate is less than or equal to a specified maximum threshold, the calibration may be indicated as valid at block 3118. If the percentage of the coefficient of variation for a calibrator replicate exceeds a specified threshold, the calibration may be determined to be invalid at block 3126.

Figure 32:
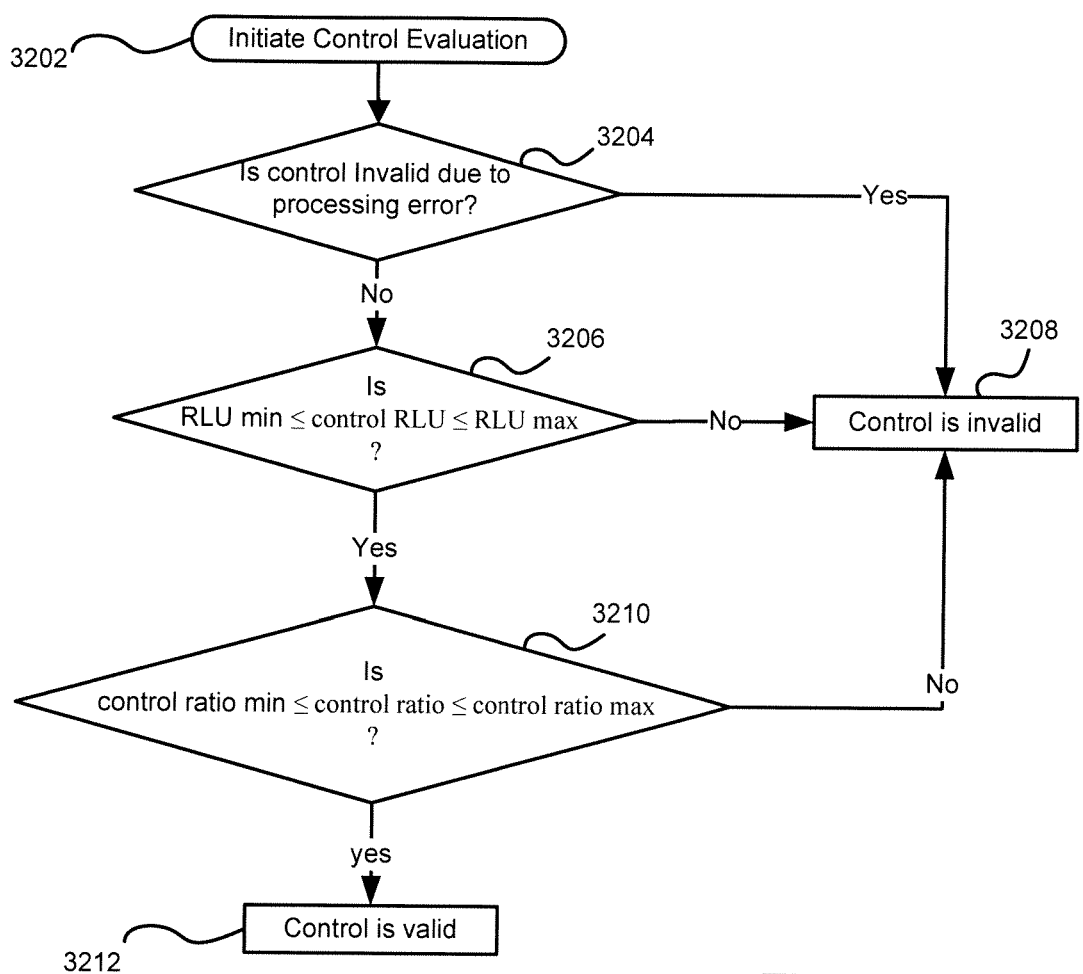
FIG. 32 depicts a method for assay control evaluation, according to an embodiment.

FIG. 32 depicts a method for assay control evaluation according to an embodiment. At block 3202 control evaluation may be initiated.

At block 3204 it may be determined whether a control is invalid due to a processing error. If a control is invalid due to a processing error, the control may be indicated as invalid at block 3208. If a control is not invalid due to a processing error the method may continue at block 3206.

At block 3206 the Relative light Unit (RLU) of a control may be compared against specified minimum and maximum values. If the RLU value of the control falls within specified values the method may continue at block 3210. If the RLU value of the control falls outside of specified values, the control may be indicated as invalid at block 3208.

At block 3210, a control ratio may be calculated for a control. The control ratio may be calculated as follows:

$$\text{Control Ratio} = \text{Well RLU}_{corrected}/\text{Assay cutoff}*$$

*assay cutoff may be specific to a specimen type.

If the control ratio falls within specified values the control may indicated as valid at block 3212. If the control ratio falls outside of specified values, the control may be indicated as invalid at block 3208.

While the invention has been described by way of examples and preferred embodiments, it is understood that the words which have been used herein are words of description, rather than words of limitation. Changes may be made, within the purview of the appended claims, without departing from the scope and spirit of the invention in its broader aspects. Although the invention has been described herein with reference to particular means, materials, and embodiments, it is understood that the invention is not limited to the particulars disclosed. The invention extends to all equivalent structures, means, and uses which are within the scope of the appended claims.

What is claimed is:

1. A method comprising:
   receiving an order to process a plurality of biological samples in a pre-analytical instrument and an analytical instrument;
   creating a worklist, wherein the worklist includes a sample identifier and an assay protocol assigned to each of the plurality of biological samples;
   instructing a user interface device to display information in the worklist; and
   monitoring the pre-analytical instrument and the analytical instrument during processing of the biological samples, wherein the monitoring comprises:
      identifying one or more biological samples that are not being processed by the pre-analytical instrument or the analytical instrument in accordance with the assay protocols associated with those biological samples in the worklist;
      instructing the user interface device to display an error notification, wherein the error notification provides at least one sample identifier associated with at least one of the identified biological samples; and
      automatically interrupting the processing of the at least one of the identified biological samples.

2. The method of claim 1, wherein the error notification further provides one or more conditions that the at least one identified biological sample failed to meet.

3. The method of claim 1 further comprising:
   sending remote diagnostic information to one or more external report systems, wherein the remote diagnostic information includes one or more indications of validity for one or more assay results.

4. The method of claim 1, wherein the monitoring further comprises:
   marking the at least one of the identified biological samples as invalid.

5. The method of claim 4 further comprising:
   triggering reflex testing of at least one of the identified biological samples that was marked as invalid during the monitoring.

6. The method of claim 5 wherein the triggering is performed in response to a user input control.

7. The method of claim 1, wherein the monitoring further comprises:
   determining whether there is a valid calibration for one or more biological samples processed by the analytical instrument; and
   marking one or more biological samples as invalid when there is no valid calibration for those biological samples.

8. The method of claim 7, wherein the determination of whether there is a valid calibration for one or more biological samples comprises:
   evaluating a plurality of calibrator replicates, wherein each of the calibrator replicates is associated with at least one calibration.

9. The method of claim 8, wherein a calibration is invalid when two or more calibrator replicates are invalid.

10. The method of claim 9, wherein the determination of whether there is a valid calibration for one or more biological samples further comprises:
    marking one or more of the calibrator replicates as invalid when those calibrator replicates have one or more processing errors.

11. The method of claim 10, wherein the determination of whether there is a valid calibration for one or more biological samples further comprises:
    measuring a relative light unit (RLU) for one or more of the calibrator replicates; and
    comparing the measured RLUs for those calibrator replicates with one or more predetermined values.

12. The method of claim 11, wherein the determination of whether there is a valid calibration for one or more biological samples further comprises:
   marking one or more of the calibrator replicates as invalid when the measured RLUs for those calibrator replicates are outside one or more predetermined ranges.

13. The method of claim 12, wherein the determination of whether there is a valid calibration for one or more biological samples further comprises:
   calculating a mean, a standard deviation, and a percentage of a coefficient of variation (CV) for one or more of the calibrator replicates; and
   marking one or more of the calibrator replicates having a percentage of a CV that is above a first maximum CV percentage threshold as invalid.

14. The method of claim 13, wherein the determination of whether there is a valid calibration for one or more biological samples further comprises:
   identifying three or more of the calibrator replicates that are associated with the same calibration and that have not been marked as valid or invalid;
   marking one of the identified calibrator replicates as invalid, wherein the one of the identified calibrator replicates has an RLU that is an outlier;
   recalculating a mean, a standard deviation, and a percentage of a CV for each of the remaining identified calibrator replicates that were not marked as invalid; and
   marking any of the remaining identified calibrator replicates having a percentage of a CV that is above a second maximum CV percentage threshold as invalid.

15. The method of claim 7, wherein the monitoring further comprises:
   evaluating one or more assay controls.

16. The method of claim 15, wherein the monitoring further comprises:
   marking one or more biological samples as invalid when there is no valid assay control for those biological samples.

17. The method of claim 16, wherein the evaluation of the one or more assay controls comprises:
   calculating assay cutoff values.

18. The method of claim 17, wherein the evaluation of the one or more assay controls further comprises:
   calculating one or more control ratios for each of the assay controls; and
   marking any of the assay controls having a control ratio that is either below a minimum control ratio threshold or above a maximum control ratio threshold as invalid.

19. A system comprising one or more computing devices configured to:
   receive an order to process a plurality of biological samples in a pre-analytical instrument and an analytical instrument;
   create a worklist, wherein the worklist includes a sample identifier and an assay protocol associated with each of the plurality of biological samples;
   instruct a user interface device to display information in the worklist; and
   monitor the pre-analytical instrument and the analytical instrument during processing of the biological samples, wherein the monitoring comprises:
      identifying one or more biological samples that are not being processed by the pre-analytical instrument or the analytical instrument in accordance with the assay protocols associated with those biological samples in the worklist;
      instructing the user interface device to display an error notification, wherein the error notification provides at least one sample identifier associated with at least one of the identified biological samples; and
      automatically interrupting the processing of the at least one of the identified biological samples.

20. The system of claim 19, wherein the one or more computing devices are further configured such that the monitoring further comprises:
   evaluating one or more calibrators and one or more controls associated with one or more assay protocols;
   determining whether one or more assay results for one or more of the biological samples are valid based on the evaluation of the one or more calibrators and controls; and
   instructing the user interface device to display an analysis of one or more of the assay results.

21. The system of claim 20, wherein the one or more computing devices are further configured to:
   send remote diagnostic information to one or more external report systems, wherein the remote diagnostic information includes one or more indications of validity for one or more assay results.

22. The system of claim 21, wherein the remote diagnostic information includes an indication that an assay result is associated with two or more invalid calibrator replicates.

23. The system of claim 21, wherein the remote diagnostic information includes an indication that an assay result is associated with an invalid assay control.

* * * * *